United States Patent [19]
Matteucci et al.

[11] Patent Number: 5,495,009
[45] Date of Patent: Feb. 27, 1996

[54] OLIGONUCLEOTIDE ANALOGS CONTAINING THIOFORMACETAL LINKAGES

[75] Inventors: Mark Matteucci, Burlingame; Bob Jones, Daly City; Kuei-Ying Lin, Fremont, all of Calif.

[73] Assignee: Gilead Sciences, Inc., Foster City, Calif.

[21] Appl. No.: 874,334

[22] Filed: Apr. 24, 1992

Related U.S. Application Data

[63] Continuation-in-part of Ser. No. 690,786, Apr. 24, 1991, Pat. No. 5,264,562, which is a continuation-in-part of Ser. No. 559,957, Jul. 30, 1990, Pat. No. 5,264,564, which is a continuation-in-part of Ser. No. 448,941, Dec. 11, 1989, abandoned, which is a continuation-in-part of Ser. No. 426,286, Oct. 24, 1989, abandoned.

[51] Int. Cl.$^6$ .................................................. C07H 21/04
[52] U.S. Cl. ...................... 536/25.3; 536/23.1; 536/25.31
[58] Field of Search ................................ 536/25.3, 23.1, 536/25.31

[56] References Cited

U.S. PATENT DOCUMENTS 4,458,066  7/1984  Caruthers et al. .................... 536/27

FOREIGN PATENT DOCUMENTS

WO89/05853  6/1989  WIPO.
WO91/06629  5/1991  WIPO.

OTHER PUBLICATIONS

Mattencci, *Tetrahedron Letters* 31(17):2385–2388, 1990.
Mertes, M. P., and Coats, E. A., *J. Med. Chem.* (1969) 12(1):154–157.
Tittensor, J. R., *J. Chem. Soc. (Section C: Organic Chemistry)* (1971) 15:2656–2662.
Sekine, M., and Nakanishi, T., *J. Org. Chem.* (1989) 54:5998–6000.
Samukov, V. V., and Ofitsrov, V. I., *Chem. Abstracts* (1983) 98:547 (abstract no. 161094x).
Veeneman, G. H., et al., *Chem. Abstracts* (1991) 114:699 (abstract no. 7074h).
Agarwal et al., *Nucleic Acids Res.* (1979) 6:3009–3024.
Agarwal et al., *Proc. Natl. Acad Sci.* (1988) 85:7079–7083.
Miller et al., *Biochemistry* (1981) 20:1874–1880.
Marcus–Secura et al., *Nucleic Acids Res.* (1987) 15:5749–5763.
Jayaraman et al., *Proc. Natl. Acad. Sci.* (1981) 78:1537–1541.
Coull et al., *Tetrahedron Letters* (1987) 28(7):745–748.
Stirchak et al., *J. Organ. Chem.* (1987) 52:4202–4206.
Cosstick et al., *Tetrahedron Letters* (1989) 30:4693–4696.
van der Krol et al., *Biotechniques* (1988) 6(10):958–976.
Stein et al., *Cancer Res.* (1988) 48:2659–2668.

*Primary Examiner*—W. Gary Jones
*Assistant Examiner*—Scott Houtteman
*Attorney, Agent, or Firm*—Morrison & Foerster

[57] ABSTRACT

Modified oligomers containing at least one internucleoside linkage of the formula $Y^1CX_2y^2$ wherein at least one of $Y^1$ and $Y^2$ is sulfur and the other is oxygen and wherein each X is the same or different and is a stabilizing substituent are disclosed. These oligomers show superior binding properties and are thus useful for binding target substances in analytical uses. Also disclosed are improved methods for synthesis of oligomers containing linkages of the general formula —$YCX_2Y$— wherein each Y may be independently oxygen or sulfur.

1 Claim, 1 Drawing Sheet

OLIGONUCLEOTIDE ANALOGS CONTAINING THIOFORMACETAL LINKAGES

This application is a continuation-in-part of Ser. No. 07/690,786, filed Apr. 24, 1991, now U.S. Pat. No. 5,264,562 which is continuation-in-part of Ser. No. 07/559,957, filed Jul. 30, 1990, now U.S. Pat No. 5,264,564 which is a continuation-in-part of Ser. No. 07,448,941, filed Dec. 11, 1989, now abandoned which is a continuation-in-part of Ser. No. 07/426,286, filed Oct. 24, 1989, now abandoned.

TECHNICAL FIELD

The application relates to the field of oligonucleotides containing novel linkages and methods for their synthesis. The invention includes biologically functional oligomers or derivatives thereof wherein at least one linkage between adjacent nucleosides comprises a linkage of the formula $Y^1$—$CX_2$—$Y^2$, wherein one of $Y^1$ and $Y^2$ is oxygen and the other is sulfur. Also, the invention relates to methods to prepare oligonucleotides containing internucleoside linkages of the formula —$YCX_2Y$—, wherein each Y is independently O or S and each X is a noninterfering stabilizing substituent.

BACKGROUND ART

PCT application WO 91/06629, published 16 May 1991 and assigned to Gilead Sciences Inc., describes modified oligomers and derivatives thereof which contain nucleotide sequences useful in binding a biological moiety wherein the modification comprises substitution for one or more linkages between individual nucleotide residues, a linkage of the formula —$YCX_2Y$—, wherein each Y is independently O or S and wherein each X is independently chosen and is a stabilizing substituent. This application, the disclosure of which is incorporated herein by reference, describes these oligomers and their derivatives, and the manner in which they are useful in a variety of contexts by virtue of the ability of the oligomers to bind various biological moieties. These oligomers are therefore useful, for example, as diagnostic agents.

DISCLOSURE OF THE INVENTION

The invention relates to oligomers containing at least one thioformacetal internucleoside linkage and to improved methods for the synthesis of oligonucleotides containing at least one internucleoside linkage of the formula —$YCX_2Y$— wherein each Y is independently O or S and wherein each X is a stabilizing substituent. As set forth in the above-referenced PCT application, these oligomers can be prepared with achiral linkages when both X are identical.

Thus, in a first aspect, the invention is directed to a biologically functional oligomer or derivative thereof wherein at least one linkage between adjacent nucleosides is of the formula $Y^1$—$CX_2$—$Y^2$, wherein one of $Y^1$ and $Y^2$ is S and the other is O and wherein $Y^1$ is understood to be attached to the 3' position of a nucleoside residue and $Y^2$ to the 5' position of the adjacent nucleoside residue. This linkage is designated herein 5'-$Y^1$—$CX_2$—$Y^2$-3'. Particularly preferred is the embodiment wherein $Y^1$ is sulfur and $Y^2$ is oxygen, i.e., wherein said linkage is of the formula 5'-$SCX_2O$-3'.

Stated another way, the invention is directed to compounds of the formula

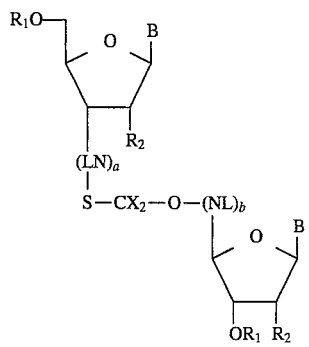

Formula 1 wherein each N is a nucleotide residue of the formula

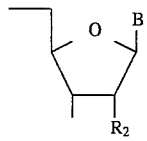

wherein each L is an internucleoside linkage that links the 3' position of one nucleoside residue to the 5' position of the adjacent nucleoside residue;

each B is independently a purine or pyrimidine residue or an analogous form thereof;

each X is independently a stabilizing group;

each $R_1$ is independently hydrogen, $PO_3^{2-}$, a protecting group, a phosphorous-containing moiety suitable for nucleotide coupling, or comprises a solid support;

each $R_2$ is independently hydrogen, hydroxyl, fluorine, O-alkyl(1-6C), O-allyl(1-6C), S-alkyl(1-6C), or S-allyl(1-6C); and a and b are independently integers of 0–100 provided that the sum of a and b is from 0 to 100, with the proviso that the —S—$CX_2$—O— nucleotide linkage links the 3' position of one nucleoside residue to the 5' position of the adjacent nucleoside residue.

Thus, in formula 1, each L is independently

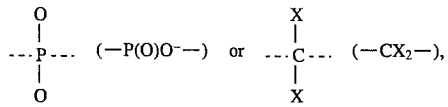

or is a conventional phosphodiester substitute (including but not limited to —P(O)S—, —P(O)$NR_2$—, —P(O)R—, or —P(O)OR'—; —CO— or —$CNR_2$— wherein R is H or alkyl (1-6C) and R' is alkyl (1-6C)).

In additional aspects, the invention is directed to intermediates in the synthesis of the compounds of the invention as well as to methods which may enable user of these compounds in assay systems and diagnosis.

The improved synthesis methods are specifically applicable to oligomers which contain linkages of the formula —$OCX_2O$—, 5'-$SCX_2O$-3'; —$OCF_2O$—, and —$OC(CH_2CH_2OCH_2CH_2)O$—.

Accordingly, in another aspect, the invention is directed to a method to synthesize an oligomer containing a 5'-$SCX_2O$-3' linkage, which method comprises reacting a first nucleoside or oligonucleotide containing the substituent $ClCX_2O$— at the 5' carbon with a second nucleoside or oligonucleotide containing an SH substituent at a 3' carbon in the presence of base to obtain a linkage of the formula —$SCX_2O$— between the 3' carbon of said second nucleoside or oligonucleotide to the 5' carbon of said first nucleoside or oligonucleotide..

In another aspect, the invention is directed to a method to prepare the required derivatized first nucleoside or oligonucleotide by reacting said first nucleoside or oligonucleotide containing OH as the substituent to the 5' carbon with paraformaldehyde and HCl.

In a second aspect, the invention relates to a method to link a first and second nucleoside through a linkage of the formula 5'-SCH$_2$O-3', which comprises treating a first nucleoside or oligonucleotide containing a substituent of the formula CH$_3$SCH$_2$O at the 5' position and protected, for example, by a substituent of the formula OSiMe$_2$Tx at the 3' position with a second nucleoside or oligonucleotide containing SH at the 3' position, and protected at the 5' position with bromine in the presence of base.

In still another aspect, the invention is directed to a method to link a first nucleoside or oligonucleotide with a second nucleoside or oligonucleotide through a linkage of the formula —OCF$_2$O—, which method comprises treating the first nucleoside or oligonucleotide protected in the 5' position with thiocarbonylimidazole in the presence of acetonitrile to obtain a 3'-derivatized intermediate followed by treating said intermediate with said second nucleoside or oligonucleotide protected in the 3' position in the presence of acetonitrile to obtain said first nucleoside or oligonucleotide linked through a —OCSO— linkage to said second nucleoside or oligonucleotide, followed by treating said linked nucleosides or oligonucleotides first with diethylaminotrifluorosulfur in the presence of acetonitrile and then with base.

In still another aspect, the invention is directed to a method to link a first nucleoside or oligonucleotide with a second nucleoside or oligonucleotide through a linkage of the formula —OC(CH$_2$CH$_2$OCH$_2$CH$_2$)O—, which method comprises treating a first nucleoside protected, for example, by a benzoyl substituent at the 3' position with 2,3-dihydro-4-methoxypyran to obtain said first nucleoside or oligonucleotide derivatized at the 5'-position with a 4-methoxytetrahydropyran-4-yl substituent; reacting the derivatized first nucleoside or oligonucleotide with a 5'-protected second nucleoside or oligonucleotide to obtain said tetrahydropyran ketal linkage of the formula —OC(CH$_2$CH$_2$OCH$_2$CH$_2$)O—.

Finally, in another aspect, the invention is directed to an improvement in the method to link oligonucleosides through a linkage of the formula —OCH$_2$O, which method comprises treating the first nucleoside or oligonucleotide derivatized at a 3' position with the substituent of the formula —OCH$_2$SCH$_3$ with a second nucleoside or oligonucleotide protected at the 3' position, for example, with the substituent OSiMe$_2$Tx, the improvement comprising reacting said nucleosides or oligonucleotides with bromine in the presence of 2,6-diethylpyridine and molecular sieves.

MODES OF CARRYING OUT THE INVENTION

A. Definitions

Figure 1:
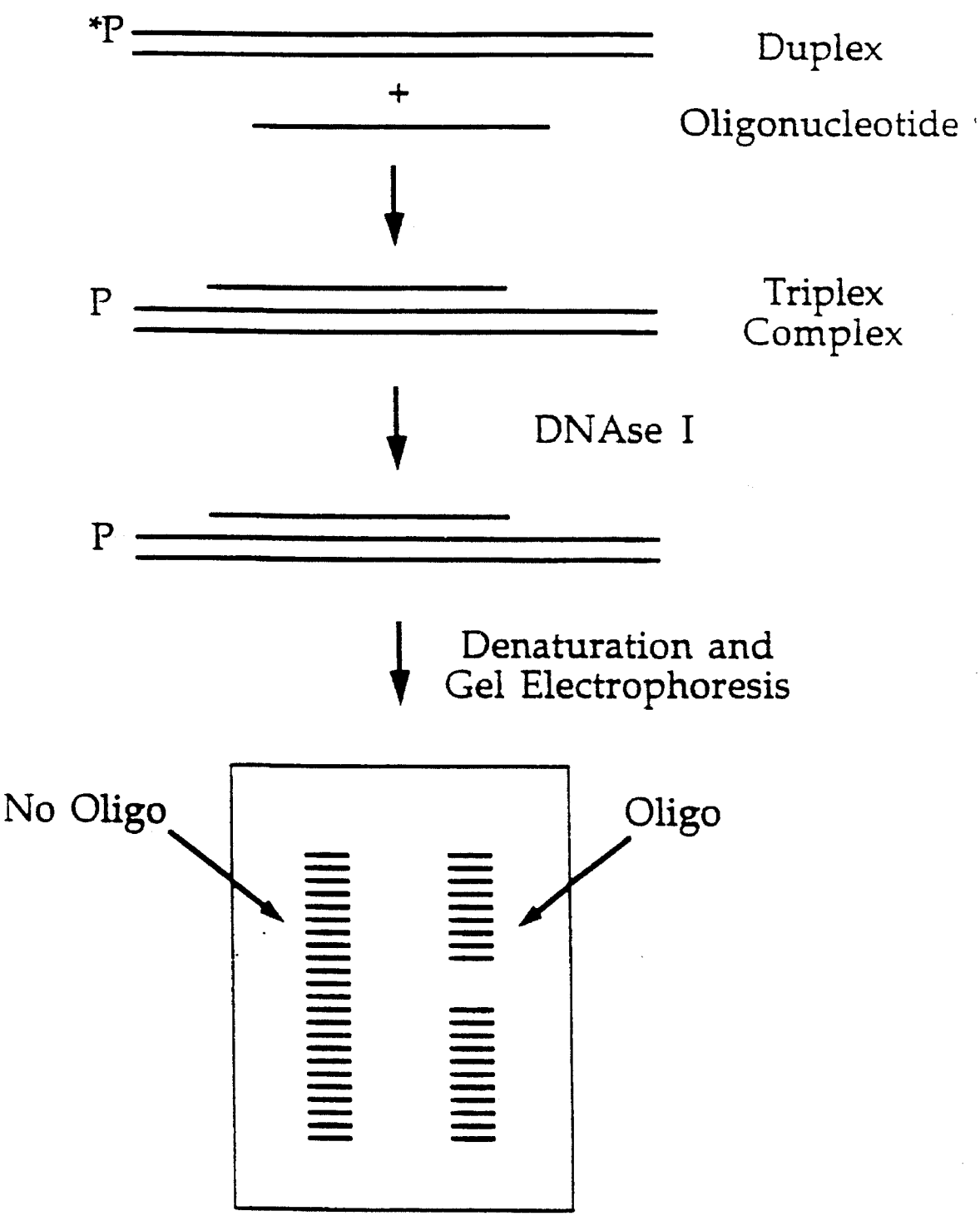
FIG. 1 shows an outline of, and idealized results of, the footprint assay for DNA-duplex binding.

The binding may be by conventional base pair complementarity, or, for example, in the case of binding to DNA duplexes, through specific interactions in the major groove of the double helix. Specific binding to other targets, such as proteins, may also be accomplished.

In addition the oligomers of the invention are useful in various diagnostic techniques which rely on specific binding of the oligonucleotide to a target substance as well as in use as probes, generally, to detect the presence, absence or amount of target substance.

"Oligomers" or "oligonucleotides" includes sequences of more than one nucleotide and specifically includes short sequences such as dimers and trimers.

"Derivatives" of the oligomers include those conventionally recognized in the art. For instance, the oligonucleotides may be covalently linked to various moieties such as intercalators, substances which interact specifically with the minor groove of the DNA double helix and other arbitrarily chosen conjugates, such as labels (radioactive, fluorescent, enzyme, etc.). These additional moieties may be (but need not be) derivatized through the —YCX$_2$Y— type linkage as part of the linkage itself. For example, intercalators, such as acridine can be linked through an —Y—CH$_2$—Y— attached through any available —OH or —SH, e.g., at the terminal 5' position of RNA or DNA, the 2' positions of RNA, or an OH or SH engineered into the 5 position of pyrimidines, e.g., instead of the 5 methyl of cytosine, a derivatized form which contains —CH$_2$CH$_2$CH$_2$OH or —CH$_2$CH$_2$CH$_2$SH in the 5 position. A wide variety of substituents can be attached, including those bound through conventional linkages. Accordingly any —OH moieties in the oligomer of formula (1) may be replaced by phosphonate groups, protected by standard protecting groups, or activated to prepare additional linkages to other nucleotides, or may be bound to the conjugated substituent. The 5' terminal OH is conventionally phosphorylated; the 2'-OH or OH substituents at the 3' terminus may also be phosphorylated. The hydroxyls may also be derivatized to standard protecting groups. In addition, specifically included are the 2'-derivatized forms disclosed in PCT application WO 91/06556.

In the oligomers of the invention, the conventional phosphodiester linkage may be replaced by alternative linking groups as long as one linkage is of the form —YCX$_2$Y—. These alternative linking groups include, but are not limited to embodiments wherein the linkage is of the form —Y—Z—Y— wherein Z is P(O)S, P(O)NR$_2$, P(O)R, P(O)OR', CO, or CNR$_2$, wherein R is H or alkyl (1- 6C) and R' is alkyl (1- 6C). Not all Z in the same oligomer need to be identical.

Purines and pyrimidines include any of those generally known in the art, including those conventionally found in RNA and DNA (A, T, G, C, U) and others, many of which are used as chemotherapeutic agents. An exemplary but not exhaustive list includes 4-acetal cytosine, 5-(carboxyhydroxylmethyl) uracil, 5-fluorouracil, 5-bromouracil, 5-carboxymethylaminomethyl- 2-thiouracil, 5-carboxymethylaminomethyluracil, dihydrouracil, inosine, N6-isopentenyladenine, 1-methyladenine, 1-methylpseudouracil, 1-methyl guanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl- 2-thiouracil, beta-D-mannosylqueosine, 5'methoxycarbonylmethyluracil, 5-methoxyuracil, 2-methylthio-N 6-isopentenyladenine, uracil-5-oxyacetic acid methylester, uracil-5-oxyacetic acid, wybutoxosine, pseudouracil, queosine, 2-thiocytosine, 5-methyl- 2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine. A particularly preferred pyrimidine is 5-methylcytosine.

The invention is directed to new compounds and intermediates in their production, as well to methods to synthesize these compounds and their intermediates. In general, the invention compounds show enhanced stability with respect to nucleases by virtue of their modified linkages, as well as enhanced ability to permeate cells. Desirably, multiple phosphodiester linkages in the unmodified oligonucleotides are substituted by corresponding —Y—CX$_2$—Y— linkages. Though it is preferred that these substituent linkages be non-chiral in nature to enhance the ability to hybridize, useful compounds of the invention include those where each X is chosen independently. Thus chiral forms may also be used, and where multiple formacetal/ketal or analogous thio-linked linkages occur in the oligonucleotide, a number of embodiments of X— may be included.

As stated above, in the linking moiety —YCX$_2$Y—, one or both of the Y is sulfur and any other is O Particularly preferred is that embodiment of the form 5'—SCX$_2$O-3'. In this designation, the linkage is that wherein sulfur is bound to the 3' position of one nucleoside and oxygen is bound to the 5' position of the adjacent nucleoside. Thus the designation 5'—Y$^1$CX$_2$Y$^2$-3' indicates a dimer or longer oligonucleotide in which the 5' designation indicates the 5' terminus of the dimer or oligonucleotide and the 3' designation indicates the 3' terminus of the dimer or oligonucleotide.

The presence of sulfur in the linkage of the formula —YCX$_2$Y— may be advantageous in that the length of the carbon-sulfur bond corresponds more closely to the length of the phosphorus-oxygen bond in the native oligonucleotide. Furthermore, greater scope is possible in connection with the substituent X groups as further described below, since the thio analogs are more stable to hydrolysis, especially under acidic conditions. In addition, the preparation reactions may proceed more smoothly due to the enhanced nucleophilicity of the SH group in the intermediates.

For ease in representation, the structure of the "wild type" oligonucleotides (and their derivatives as defined above) will sometimes be shown in the following shorthand form:

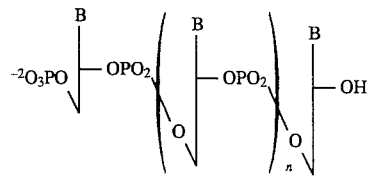

In this representation, B represents the usual purine or pyrimidine bases such as A, T, C, G as well as any modified forms of these bases that might be desirable in a particular therapeutic or compound. It is also understood that for some particular applications, one or more of these "B" groups may be replaced by any arbitrary substituent so long as that substituent does not interfere with the desired behavior of the oligomer. In most cases, these may be replaced by other purines or pyrimidine substituents as defined above.

The corresponding shorthand for one group of the modified oligomers of the invention is, similarly,

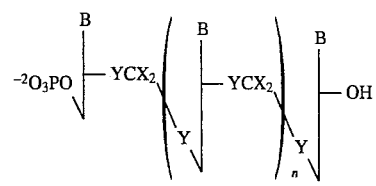

where similar remarks apply to the nature of B and to the possibility of derivatization. In addition, as the linkages of the invention are stable to nuclease attack, in addition to modified forms of DNA, similarly modified forms of RNA are included in the invention.

It should be clear that the invention compounds are not limited to oligomers of homogeneous linkage type, and that alternating or randomly distributed phosphodiester (or other substituted) and —YCX$_2$Y— linkages are contemplated. Since the oligomers of the invention can be synthesized one nucleotide residue at a time, each individual linkage, and the nature of each individual "B" substituent can be chosen at will. Thus, the linkage of the formula —YCX$_2$Y— may be included alternating with conventional diester linkages or alternative linkages or may be randomly included in the oligomer, or may assume any pattern desired consistent with the intended use.

X must be of such a nature so as to be stabilizing of the substitute invention link. For embodiments wherein both Y are O— i.e. —OCX$_2$O—; alkyl substituents are unworkable unless one X attached to the ketal C is compensated by a high electron withdrawing ability of the other. However, for embodiments of the present invention of the formula —Y$^1$CX$_2$Y$^2$— wherein at least one of Y$^1$ and Y$^2$ is S, the presence of alkyl groups as embodiments of X is tolerated. Preferred embodiments of X thus include H, alkyl (1-6C), halide, carboxyl or an alkyl (1-6C) ester or alkyl (1-6C) amide thereof; —SOR or —SO$_2$R wherein R is an organic residue, typically alkyl (1-6C); —CN, CHF$_2$ or —CF$_3$. Other embodiments of X include electron withdrawing groups separated from the linking C of —YCX$_2$Y— by 1-3 methylene groups; i.e., X is —(CH$_2$)$_n$W wherein n is 1-3 and W is an electron withdrawing substituent. In general, the greater the value of n, the more electron withdrawing W should be. Typical embodiments of W include halo, carboxyl or an alkyl (1-6C) ester or alkyl (1-6C) amid thereof, phosphate or phosphonate, or an alkyl (1-6C) ester thereof, SOR or SO$_2$R, wherein R is alkyl (1-6C), CN, NO$_2$, CF$_3$, CHF$_2$, OH, OR (wherein R is alkyl 1-6C) and primary, secondary, or tertiary amines. W may further contain a heteroatom, such as hydroxymethyl, or substituted hydroxymethyl, such as those embodiments wherein W is OCH$_2$OCH$_2$OH, or e.g., OCH$_2$CH$_2$OH.

In addition, both X together may constitute a cyclic substituent containing at least one heteroatom. In these embodiments, CX$_2$ may thus be, for example,

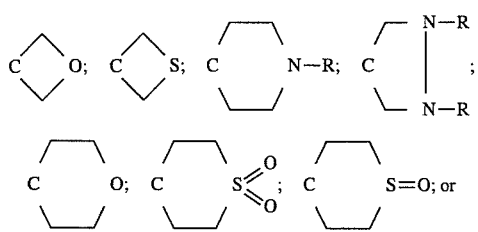

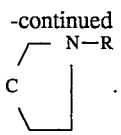

Suitable X substituents include, therefore, —H, F, —Cl, —Br, —COOH, —COOCH$_3$, —COOCH(CH$_3$)$_2$, —CONHCH$_3$, —CHF$_2$, —CF$_3$, —CH$_2$COOCH$_3$, —CH$_2$CONHCH$_2$CH$_3$, —CH$_2$CH$_2$COOH, —CH$_2$CH$_2$NH$_2$, —CH$_2$CH$_2$NHCH$_2$CH$_3$, —CH$_2$CH$_2$CF$_3$, and so forth. If the Xs are different, both Xs together must confer sufficient electron withdrawing ability to stabilize the oligomer.

Particularly preferred are embodiments wherein both X are H or F or where both X taken together are —(CH$_2$)$_2$O(CH$_2$)$_2$.

The linkages of the invention wherein one or more of the linking oxygens is replaced by a sulfur are inherently more stable than their oxygen containing analogs. Thus, linkages of the formula —OCX$_2$S—, —SCX$_2$O—, and —SCX$_2$S—, are less demanding of electron withdrawal than the linkage —OCX$_2$O—. These may be alkyl, or even phenyl, so long as the phenyl contains an electron withdrawing substituent in the appropriate position—e.g. 2-nitro, 4-nitro or 2,4-nitrophenyl. Of course, the linkage —SCX$_2$S— is the most tolerant of electron donation. The extent to which the spectrum of substituents for X can be extended into those which are potentially electron donating can readily be determined by simple assays of stability of the resulting product, and this determination, and a good deal of predictability of the tolerance of these linkages, is within the ordinary skill of the art. However, embodiments wherein both X and H are preferred.

It should further be noted that if X, itself, contains a functional group, X can be used to tether desired moieties useful as adjuncts in therapy, for example, intercalators or minor groove reactive materials, such as netropsin and its derivatives, anthramycin, quinoxaline antibiotics, actinomycin, and pyrrolo (1–4) benzodiazepine derivatives.

The oligomers of the invention may contain an arbitrary member of the —YCX$_2$Y— linkages of the invention. These may be identical to each other or different by virtue of the embodiments chosen for X, and/or by virtue of the choice of —OCX$_2$O—, —SCX$_2$O—, —OCX$_2$S— or —SCX$_2$S—. Since the oligomers are prepared sequentially, any pattern of linkage types, base substituents, and saccharide residues may be used.

In some preferred embodiments, the —YCX$_2$Y— linkages alternate in a regular pattern. Preferred embodiments include oligomers which contain, for example, a series of 3–8, —YCX$_2$Y— linkages alternating regularly with respect to regions of diester linkages. Particularly preferred are alternating structures wherein a —YCX$_2$Y— linkage is followed by a phosphodiester followed by a —YCX$_2$Y— followed by a phosphodiester, etc., so that there is a one-by-one alternation of the two types of linkages. Additional alternatives might include, for example, a thioformacetal type linkage followed by two diesters followed by a single thioformacetal type linkage followed by two diesters, etc. A variety of regularly variant patterns is readily derived.

It is also clear that arbitrary modifications may be made to one or more of the saccharide residues; for example, xylose or deoxyxylose residues or hexose residues may be substituted. However, for the most part, the standard 3'–5' nucleotide linkage between ribosyl or deoxyribosyl residues is most convenient. Where this is the case, further abbreviation of the structures may be used. For example, in standard DNA (or RNA) the sequences are generally denoted by the sequence of bases alone, such as, for example, ATG CGC TGA. In general, it is simply stated in advance whether this represents an RNA or DNA sequence. In the compounds of the invention, similar notation will be used for modifications of otherwise physiological DNA or RNA molecules but the phosphodiester linkages replaced by the —YCX$_2$Y— type will be noted in the structure. Thus, 5'-ATG (SCX$_2$O) GTCA (SCX$_2$O ) AGG-3' (SEQ ID NO: 1) indicates an oligonucleotide ATGGTCAAGG (SEQ ID NO: 2) with two of the phosphodiester linkages modified in the noted positions. This is further abbreviated generally below as †. Thus the designation 5'ATG†GTCA†AGG3' may also be used.

Similarly, like the unmodified counterparts, the oligonucleotides of the invention are capable of binding specific targets in diagnostic or analytical assays. The manner of conduct of such assays using oligonucleotides as specific binding reagents is well-known in the art.

B. Utility and Administration

Accordingly, the modified oligomers of the invention are useful in, diagnostic and research contexts. In therapeutic applications, —as described above, includes targeting a specific DNA or RNA sequence through complementarity or through any other specific binding means, for example, sequence-specific orientation in the major groove of the DNA double-helix, or any other specific binding mode, or targeting any biologically relevant molecule, such as a protein.

In addition the oligomers of the invention may be used as diagnostic reagents to detect the presence or absence of the target sequences to which they specifically bind. Such diagnostic tests are conducted by hybridization through base complementarity, triple helix formation, or complex formation with other targets which is then detected by conventional means. For example, the oligomers may be labeled using radioactive, fluorescent, or chromogenic labels and the presence of label bound to complex detected. Alternatively, the presence of a double or triple helix or other complex may be detected by antibodies which specifically recognize these forms. Means for conducting assays using such oligomers as probes are generally known.

Finally, it is understood that the oligomers can be derivatized to a variety of moieties which include, intercalators, chelators, lipophilic groups, label, or any other substituent which modifies but does not materially destroy the oligomeric character of the backbone.

C. Synthesis

PCT application WO 91/06629 sets forth schemes 1–4, reproduced below, which specifically provide methods to obtain dimers with the linkage —OCH$_2$O— (reaction scheme 1); to obtain a nucleoside with an SH substituent in the 5' position (reaction scheme 2); to obtain a monomer with a blocked S— substituent at the 5' position and a substituent of the formula —OCH$_2$SMe at the 3' position (reaction scheme 3); and the condensation of this monomer with the monomer prepared in reaction scheme 2 to obtain a dimer containing an internucleoside linkage of the formula 3'-OCH$_2$S-5' (reaction scheme 4); a description of methods which are analogous to those described in PCT application WO 91/106629 for the preparation of oligomers with linkages of the formulas 5-SCX$_2$O-3' and —SCX$_2$S— were also described therein.

In addition to the compounds of the present invention, the present application is directed to an improvement to the steps shown in reaction scheme 1 and to the methods of synthesis shown in reaction schemes 5–8. All of reaction schemes 1–4 and a description thereof are repeated here for convenience.

Schemes 1–4 and 8 show structural formulas as traditionally drawn. In schemes 5–7, and is an alternative representation of scheme 8, notation is substituted wherein the indicated nucleoside is designated by the corresponding starred base. Thus, the starting materials in Reaction Scheme 1 would be shown as 5'DMTO-T*—OH-3' and 5'HO—T*—OSiMe₂Tx 3', and the product of step 3 as 5'HO—T*—OCH₂O—T*—OSiMe₂Tx 3'. Generally, the single reactants are represented 5'PrO—B*—OPr 3' and the products are represented 5'PrO—B*—YCX₂Y—B*—OPr 3' wherein B* represents a nucleoside residue, Y and X are as above-defined, and each Pr is independently H, a protecting group, or a phosphate/phosphite reactive group.

Schemes 1–8 show illustrative procedures for preparing the oligonucleotides of the invention. In the schemes as shown, for simplicity, X is shown as H, and particular pyrimidine bases are used for illustration. Further, the schemes show the synthesis of dimers from individual nucleosides. However, these reaction schemes may be generalized for the embodiments set forth herein of X in the linkage —YCX₂Y—. Also oligonucleotides may be substituted for the nucleosides. If a protecting group is indicated on the nucleoside shown in the schemes, or referred to in the examples, the protecting group then resides at the corresponding position at the 5' or 3' terminus of the oligonucleotide.

In a preferred manner of conducting the reaction schemes at least one of the moieties to be linked is a single nucleoside, while the other may be an oligomer of arbitrary length. Thus, the illustrated linkages can be sequentially provided to obtain an oligomer of any length. If both reactants are, however, oligomers, it is preferred that at least one reactant be relatively short—for example, a dimer or trimer.

In one general approach, the oligomers (including dimers and trimers) of the invention which contain substituted formacetal/ketal linkages are coupled using a modification of the disaccharide synthesis method of Nicolaou, K. C., et al. *J Am Chem Soc* (1983) 105:2430. The nucleosides to be coupled are protected in the positions where participation in the linkage is not desired; one partner is treated with a reagent such as ClCX₂SMe in the presence of a base and in an inert solvent to form a thioacetal intermediate. This activated nucleoside is then reacted with the nucleoside to which it is to be coupled, said nucleoside protected at all positions other than the hydroxyl (or sulfhydryl) intended to form the linkage. This reaction may be conducted in the presence of N-bromosuccinimide and a sterically hindered weak base to obtain the protected dimer. The resulting suitably deprotected dimer can then be extended by repeating this conjugation. The use of this general approach to the formation of a formacetal linked trimer is shown in Reaction Scheme 1.

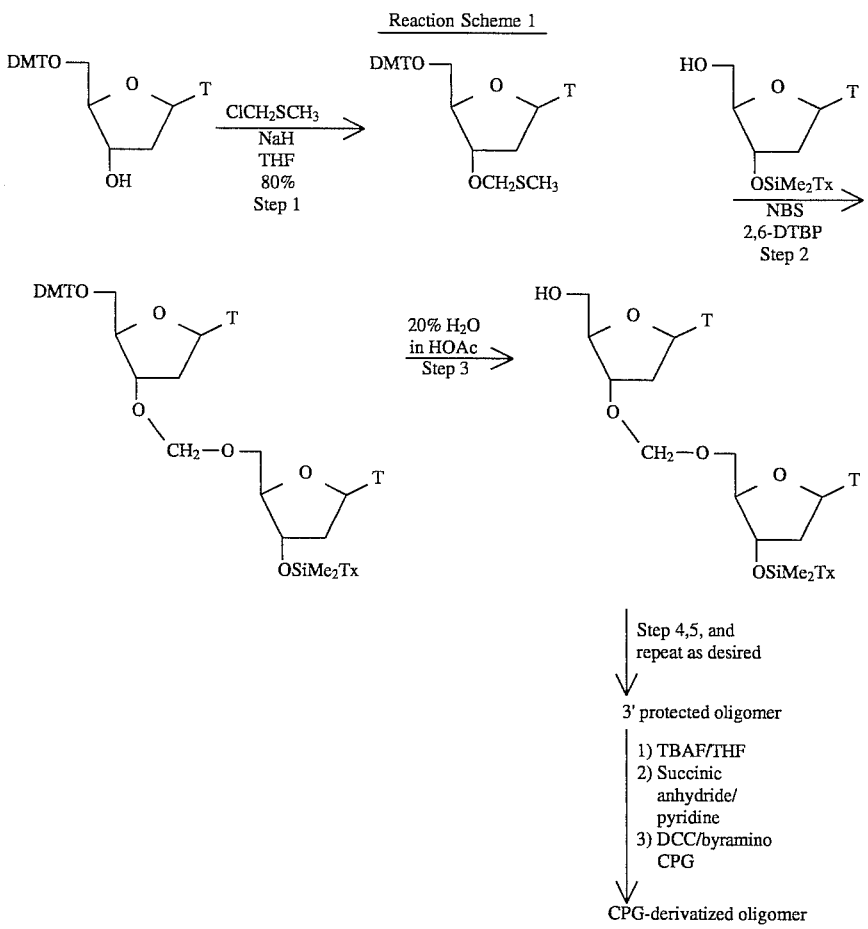

Reaction Scheme 1

In step 1, thymidine protected at the 5' position with, for example, dimethoxytrityl (DMT) is converted to the methyl thioacetal or other thioacetal. The ClCH₂SCH₃ reagent shown may be replaced by the corresponding bromide, or other thioethers of the general formula $ClCX_2SR$ or $BrCX_2SR$. The reaction in step 2 is conducted in the presence of N-bromosuccinimide (NBS) and 2,6-di-t-butylpyridine (2,6 DTBP) in methylene chloride for reaction of the thioacetal with a 5' hydroxyl of thymidine protected at the 3' position with thexyl dimethylsilyl. It should be noted that the hindered pyridine, 2,6-t-butylpyridine is required in step 2 since the less hindered dimethyl form is alkylated by the activated acetal. This results in the protected dimer containing the desired formacetal/ketal linkage. Deprotection in acid liberates the 5' position from the protecting trityl group, providing a dimer which can then be reacted with the 5'-DMT-3'— methylthioacetal as in step 2 in an additional step 4 to obtain the protected trimer, which can be deprotected as in step 3 in an additional step 5.

These steps can be repeated choosing any derivatized nucleoside for the 5'-protected 3'-derivatized reagent in a reaction analogous to step 2 to obtain oligomers of any desired length.

In a modified form of the scheme shown in Reaction Scheme 1, improved yields are obtained by utilizing, instead of NBS and 2,6 DTBP, treatment with bromine in the presence of 2,6-diethylpyridine and molecular seives, followed by treatment by tetrabutyl ammonium fluoride in a tetrahydrofuran (THF) solvent. In this alternative approach, the dimer deprotected in the 3' position is obtained, although the DMTO protection at the 5' position is retained. In general, the 5' DMTO-T*— $OCH_2SCH_3$ monomer is mixed with a slight excess of the 5'HO—T*—$OSiMe_2Tx$ monomer and is further mixed with 2,6-diethylpyridine in an inert solvent. This is followed by the addition of dissolved bromine and the mixture is stirred for several hours at room temperature. After extraction with mild base, the organic fraction is redissolved in aprotic polar solvent and treated with a solution of tetrabutyl ammonium fluoride at room temperature for 10 minutes-about 1 hour. The condensed dimer is recovered by extraction into an organic solvent from base and purified using conventional means.

Reaction Schemes 2, 3 and 4 show the production of dimers and trimers which have linkages of the form 3'-$OCX_2S$-5'. Reaction Schemes 2 and 3 show the preparation of the individual components of the dimer, Reaction Scheme 4 the dimer formation. Thymidine derivatives are also used in this example.

Reaction Scheme 2

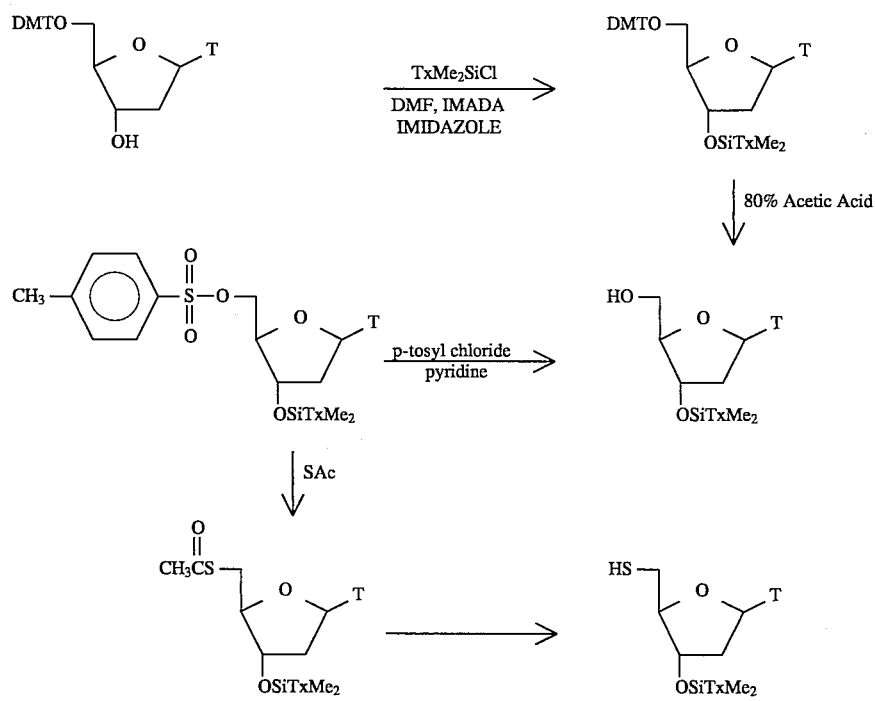

Reaction Scheme 3
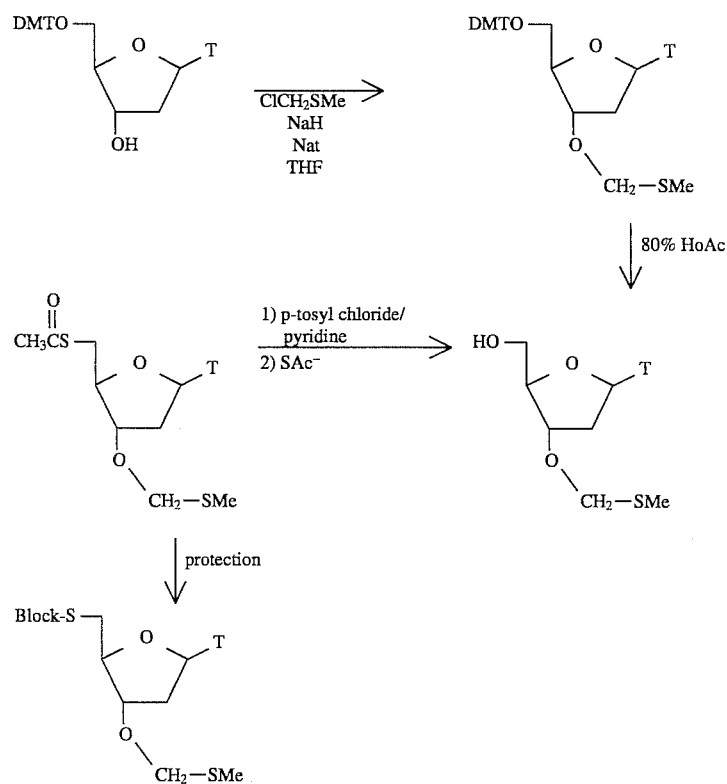
Reaction Scheme 4
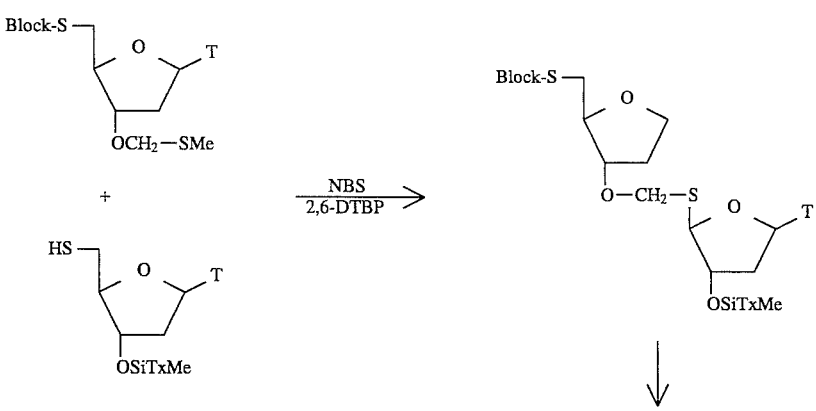

-continued
Reaction Scheme 4 protected trimer

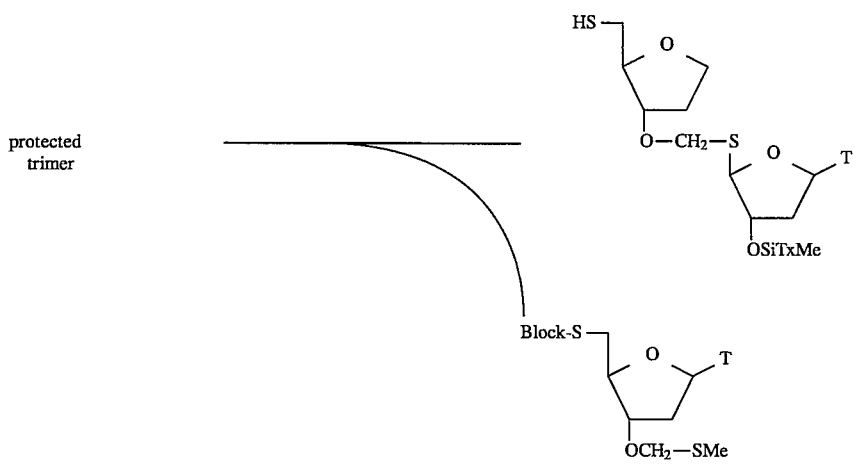

Reaction Scheme 2 describes the preparation of the 3'-protected thymidine having SH in the 5' position. As shown in the sequence of reactions, a 5' dimethoxytrityl thymidine is silylated using thexyl dimethylsilyl chloride. The resulting 3'-silylated sugar is hydrolyzed in 80% acetic acid and the 5'-hydroxy is then activated using p-tolylsulfonyl chloride in pyridine; the p-tolylsulfonyl group is then replaced using a salt of thioacetic acid as described by Reist, E., et al., *J Am Chem Soc* (1964) 29:554. The acetalthioester can be stored, and is hydrolyzed immediately prior to use to prevent disulfide formation, as described in the Reist paper.

Reaction Scheme 3 describes the activation of the 3'OH subsequent to conversion of the 5' position to a protected sulfhydryl, if desired. As shown, the 5'dimethoxytrityl protected thymidine is alkylated with chloromethylthiomethane in THF using sodium hydride as a base and sodium iodide as a catalyst. To obtain the 3'thioacetal other reagents besides chloromethylthio-methane may be used, such as chloromethylthiobenzene and chloromethyl-2-thiopyridine, or the corresponding bromides of any of the above. These may even be superior or lead to thioacetal products which have leaving groups superior to the methylthio shown. The protecting dimethoxytrityl group is then removed with 80% acetic acid, for example, and activated and converted to the thioester as was described in Reaction Scheme 2-activation with tosyl chloride, followed by treatment with a salt of thioacetic acid.

The acetal thioester may itself subsequently be used in the condensation reaction with the product of Reaction Scheme 2, but superior methods for protection of the SH are available. In one such scheme, the acetal/thio group is hydrolyzed and the resulting sulfhydryl reacted with dimethoxytrityl chloride or trimethoxytrityl chloride generating a trityl sulfide, according to the procedure of Hiskey, R. G. et al., *J Org Chem* (1966) 31:1188. Subsequent deprotection is effected under mild acid conditions. In a second approach, the hydrolyzed free SH group is reacted with dinitrophenyl sulfonyl chloride, thus generating a disulfide group, according to the method of Fontana, A., *J Chem Soc Chem Commun* (1975) 976. The disulfide can be removed with reducing agents such as mercaptoethanol or sodium borohydride. Both of these alternative schemes of protection result in a visible color when deprotection is conducted.

The protected thioacetal monomer resulting from scheme 3 is then reacted with the 3'-protected 5' sulfhydryl product of Reaction Scheme 2 as shown in Reaction Scheme 4. The components are mixed in slightly less than an equivalent of N-bromosuccinimide in the presence of an excess of a hindered base, such as 2, 6-di-t-butyl pyridine as shown. The NBS and 2,6-DTBP are first added to the blocked thioacetal and the activated 3' thioacetal thymidine is then reacted with the 5' SH thymidine. This order of addition is required to prevent the side reaction of the reagents with the 5'SH group. As for Reaction Scheme 1, improved yields are obtained by substituting treatment of the components with 2,6-diethyl pyridine and bromine ($Br_2$) for NBS and 2,6-DTBP. The resulting dimer can be extended as shown in Reaction Scheme 4, or as many times as desired by repeating the condensation reaction with another equivalent of the thioacetal.

The 3' thionucleosides are also available in the art, and can be synthesized as described by Zuckermann, R. et al., *Nucl Acids Res* (1985) 15:5305 and 3' thiothymidine has been used for the synthesis of oligonucleotides as described by Cosstick, R. et al. *Tet Lett* (1989) 30:4693–4696, cited above. The 3' thionucleosides can be converted to the dithio analogs of the acetals in a manner analogous to the first steps of Reaction Scheme 1 or Reaction Scheme 3 to provide a suitable leaving group for nucleophilic attack by either an SH or OH at the 5' position of the adjacent nucleoside, in a manner analogous to that shown in Reaction Scheme 1 or 4. Thus, in a manner analogous to the methods shown for the preparation of the formacetal/ketal and the linkage of the formula —$OCX_2S$—, dimers, trimers, and oligomers with linkages of the formulas —$SCX_2O$— and —$SCX_2S$— can be obtained.

A modified approach to obtaining the 5'-$OCX_2$S-3' (—$SCX_2O$—) linkages is shown in Reaction Scheme 5.

Reaction Scheme 5

5'MeSCH$_2$O—T*—OSiMe$_2$Tx 3'
pyridine
+
5' DMTO—T*—SH 3'

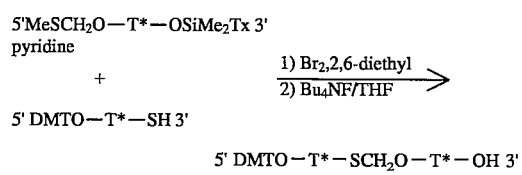

5' DMTO—T*—SCH$_2$O—T*—OH 3'

The starting material, 5'-methylthiomethyl-3'-t-butyldimethyl silylthymidine, is first prepared by reduction of 3'-t-butyldimethyl silylthymidine by a suitable hydride by reaction at room temperature followed by addition of sodium iodide and chloromethyl methyl sulfide. This reaction mixture is mixed for 1 hour at room temperature and diluted with an inert solvent and the activated, protected thymidine 5' MeSCH$_2$O—T*—OSiMe$_2$— Tx 3' is purified.

To form the dimer, 5' DMTO-T*—SH 3' is mixed with an excess of 2,6-diethylpyridine in an inert solvent. To this solution, after stirring for a suitable period at room temperature, an approximately 1M solution of bromine in inert solvent is added. This solution is also stirred for about 30 minutes and the 5'-DMT-3'-thiothymidine, dissolved in an inert solvent, is then added.

The reaction mixture is held at room temperature for 1–3 hours, preferably around 2 hours and the reaction mixture is worked up to isolate the dimer product 5' DMTO-T*—SCH$_2$O-T*—OH 3'. The reaction can be repeated as desired to form trimers or higher oligomers by rederivatizing the 3' OH of the dimer to form the silylate and deprotecting and activating the 5' position of the dimer to obtain the methyl thiomethyl ether of the formula 5' MeSCH$_2$O-T*—SCH$_2$O-T*—OSiMe$_2$Tx 3'. This is then reacted with 5' DMTO-T*—SH 3' as set forth in Reaction Scheme 5. Alternatively, corresponding dimers prepared as in Reaction Schemes 1 or 4 may be activated at the 5' position and reacted with the 5' protected, 3' SH nucleoside.

Reaction Schemes 6 and 7 show the syntheses of linkages of the formulas —OCF$_2$O— and the corresponding linkage wherein X$_2$ comprises the residue of a dioxane ring.

In Reaction Scheme 6, advantage is taken of the reactivity of thiocarbonyl imidazole to activate a free 3'-OH group in a protected thymidine nucleoside. The activated nucleoside is then condensed with a 5'-OH, 3'-protected nucleoside to obtain the dimer linked through —OCSO—. The intermediate dimer is then desulfurized and fluorinated by treatment with diethylamino trifluoro sulfur (DAST) in the presence of acetonitrile.

Reaction Scheme 6

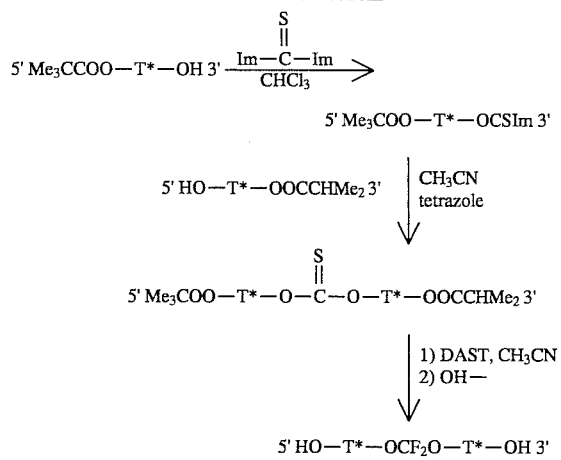

In more detail, the 5' protected thymidine is reacted with the thiocarbonylimidazole in the presence of acetonitrile under an inert atmosphere at elevated temperatures of about 60° C., for 12–24 hours, preferably about 16 hours or until reaction is complete. After cooling, the condensation product is recovered in an organic layer and treated with the 3' protected thymidine, again in the presence of acetonitrile, to obtain the —OCSO— linked dimer. The formation of dimer takes place under an inert gas in a sealed vessel at about 80° C. for about 48 hours. After dilution with inert solvent such as methylene chloride, the dimer is recovered and purified for example by column chromatography.

The purified material is then dried and desulfurized and fluorinated by treatment with DAST in the presence of dry acetonitrile under inert gas at about 40° C. for about 16 hours. The product containing the —OCF$_2$— linkage is then recovered.

Reaction Scheme 7 shows the synthesis of the dimer linked through a tetrahydropyran ketal. In Reaction Scheme 7, as shown, Bz represents benzoyl, Pv represents pivaloyl, and TSA is toluene sulfonic acid.

Reaction Scheme 7

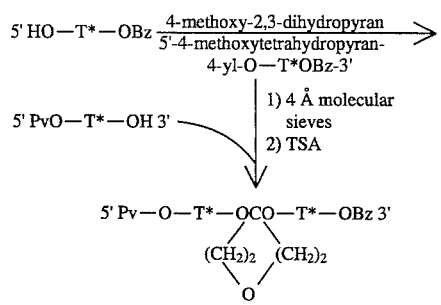

As shown generally, the 3'-benzoylthymidine is reacted with 2,3-dihydro-4-methoxypyran to obtain the 5'-derivatized 3'-benzoylthymidine. The 5' position, derivatized to the 4-methoxytetrahydropyran-4-yl substituent, is then reacted with a 5'-protected thymidine to obtain the tetrahydropyran ketal. The condensation to form the dimer is conducted in the presence of molecular sieves under inert gas with stirring at about 20° C. for about 16 hours. After this period, p-toluenesulfonic acid (which has been dried) is added to the reaction mixture and the reaction is then agitated for about 2 more hours at about 50° C. under inert gas. The reaction is cooled to about 20° C. and quenched using triethylamine. The dimer, still protected at the 5' and 3'-positions is then purified using chromatographic methods. The steps of Reaction Scheme 7 can be repeated to obtain trimers or oligomers of any length, or the dimer may be used as a synthon for extensions with other nucleosides, dimers or oligomers.

For reaction schemes wherein the resultant retains the silyl protecting group, the resulting dimer, trimer or oligomer may be desilylated with tetrabutyl ammonium fluoride (TBAF) in an inert solvent such as THF and succinylated as a convenient linker for coupling to a solid support, such as controlled pore glass (CPG). The coupled modified oligomer can be used as a starting material for standard oligonucleotide synthesis, as, for example, using H-phosphonate chemistry as described by Froehler, B., et al., *Nucleic Acids Res* (1986) 14:5399. This synthesis involves deprotection of the 5' hydroxyl using dichloroacetic acid in methylene chloride and treatment with a 5' DMT-protected base 3' phosphonate in the presence of acetal chloride/pyrimidine/acetonitrile, and repetition of this deprotection and linkage protocol for any desired number of times.

Alternatively, the liberated 3'-OH can be linked via an ester linkage to a solid support analogous to standard oligonucleotide synthesis (Matteucci, M. et al., *J Am Chem Soc* (1981) 103:3185, for extension of oligonucleotide.

Reaction scheme 8 shows an additional preferred method for the synthesis of oligomers containing a linkage of the form 5'-SCH$_2$O-3'. In the first representation, the synthesis of a dimer of thymidine (T*) and 5-methyl cytidine (C̈*) is used as illustration. In the second representation a dimer of thymidine is prepared.

Reaction Scheme 8

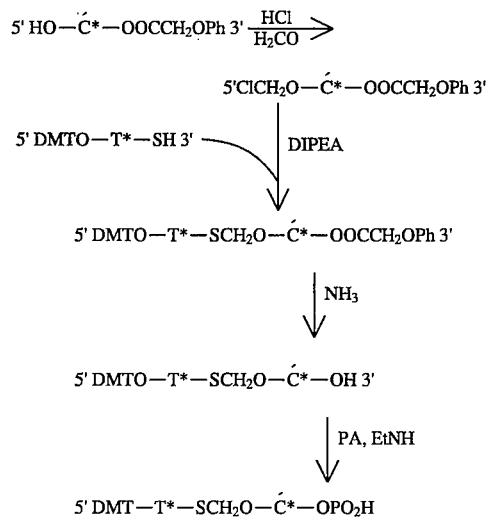

Reaction Scheme 8

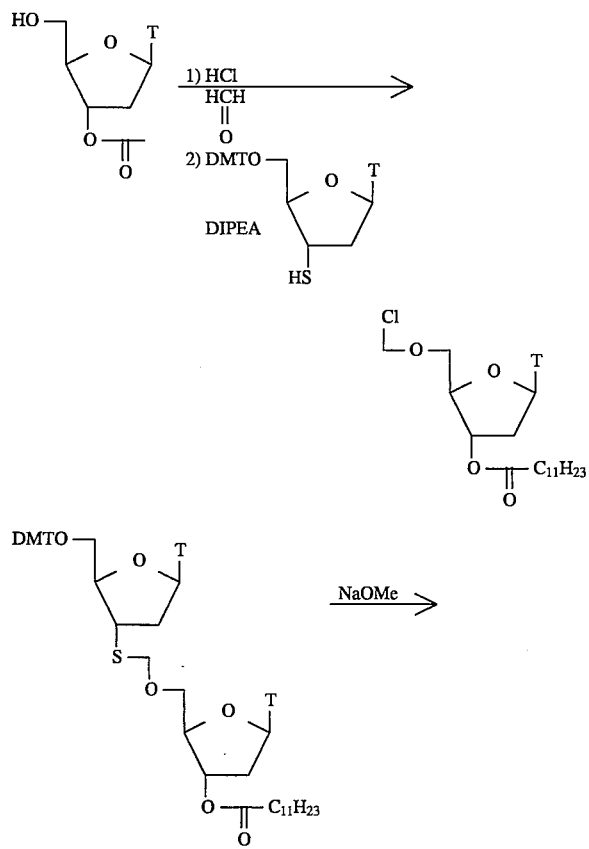

-continued
Reaction Scheme 8

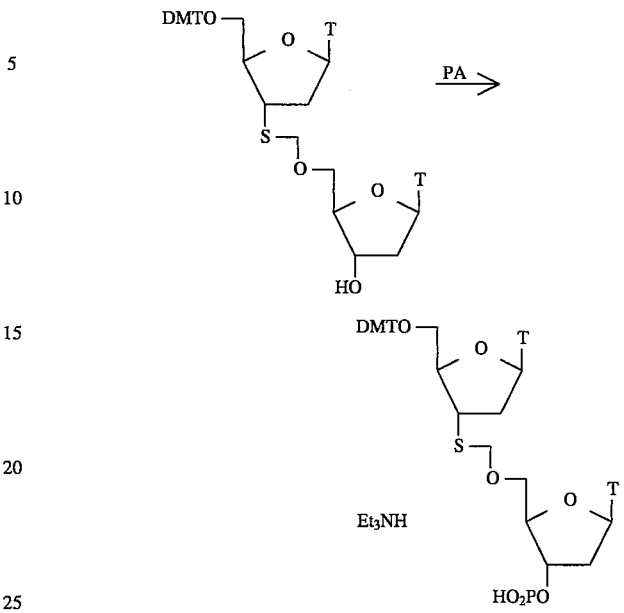

As shown in reaction scheme 8, a nucleoside protected at the 3' position by esterification is first reacted with paraformaldehyde in the presence of HCl to obtain the derivatized nucleoside containing the substituent $ClCHO_2$— at the 5' position. The nucleoside can be esterified using, for example, a long-chain alkoyl or aromatic acid, such a decoyl, hexoyl, benzoyl, or phenoxyacetyl. In this first step, the 3'-esterified nucleoside is treated with an excess of paraformaldehyde in an inert solvent at low temperature and anhydrous HCl is bubbled through the reaction mixture for one to several days. The solution is conveniently dried and the solvent removed to obtain the intermediate.

The intermediate, shown as the chloromethylether ($ClCH_2O$—) at the 5' position of the nucleoside, is then dissolved in an inert solvent. A solution of a second nucleoside protected at the 5' position, for example by DMT, and bearing an —SH substituent at the 3' position along with a base in an inert solvent, preferably diisopropylethylamine (DIPEA) is also prepared. The chloromethyl ether intermediate is added dropwise to this solution and the reaction mixture is stirred for several hours.

The reaction is stopped with base, such as aqueous sodium bicarbonate, and the organic layer is separated and dried to obtain the dimerized product having the 5'—$SCH_2O$-3' linkage and protected at the 5' and 3' positions, as above. The resulting dimer is then deprotected at the 3' position, if desired, by treatment with base, such as ammonia or sodium methoxide, and then, if to be used in standard oligonucleotide synthesis processes, activated to form the phosphonate using 2-chloro-4H-1,2,3-benzodioxaphosphorin-4-one (van Boom's reagent) (PA) in the presence of $Et_3NH$.

While all of the foregoing schemes have been described as condensations of single nucleosides to obtain dimers, it is evident that oligomers could be substituted for either or both of the monomeric nucleosides. The protective groups indicated with respect to the individual nucleosides then reappear at the relevant 3' or 5' terminus of the corresponding oligonucleotide used.

Additional —YCX$_2$Y— linkages can be inserted in the oligomer by activating to a suitable linkage forming group the dimers, trimers, pentamers, etc., obtained as set forth in Reaction Schemes 1–7 and using these as the adducts in the oligomeric chain extensions. The final product is removed from the solid support by standard procedures, such as treatment with iodine in a basic aqueous medium containing THF or other inert solvent, followed by treatment with ammonium hydroxide. Deprotection of the nucleotide bases attached to the added nucleotides is also conducted by standard procedures.

The —YCX$_2$Y— linkage can be included at any arbitrary position in an oligonucleotide by substituting for a conventional monomer in the sequential synthesis, a protected dimer containing the —YCX$_2$Y— linkage which has been synthesized as in Reaction Schemes 1 and 4–7, by supplying the dimer as a suitably protected and phosphate/phosphate-activated moiety. Thus either the 5' or 3' position of the dimer is provided with a protecting group and the other an activated form of phosphate/phosphite. The phosphate/phosphite is conveniently present as the triethylamine salt. This dimer is then incorporated at any desired location in the synthetic process using the standard steps of oligonucleotide synthesis.

Synthesis of the oligomer using standard techniques can be effected using the dimer synthons, for example, of the formula:

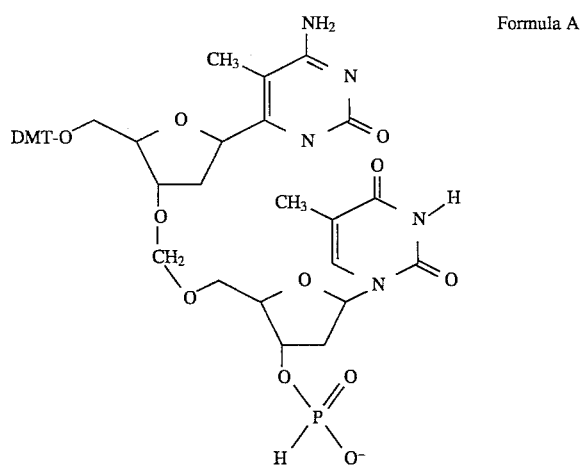

Formula A or generally of the formula 5' PrO-B*—YCX$_2$Y-B*—Opr, wherein-one of Pr is a protecting group and the other is an activated phosphate/phosphite. Utilization of a series of these synthons results in the one-by-one alternation of the formacetal and phosphodiester linkages. Extended regions containing phosphodiester linkages are easily included by extending the chain with single nucleotides; extended regions containing the formacetal/ketal type linkages are obtained by extending the dimers in protocols analogous to those set forth in Reaction Schemes 1–7.

Any DNA synthesis chemistry such as phosphoramidate or phosphonate chemistry can be used to link monomers or dimers in a manner analogous to that set forth above.

The following examples are intended to illustrate but not to limit the invention.

Preparation A

Preparation of 5' TCTCCCTCTCTTT(OCH$_2$O)T(OCH$_2$O)T-3'(SEQ. ID. NO: 3) See also: Matteucci, M.D., Tet Lett (1990) 31:2385.

Part A: Oligomer Preparation

Preparation of 5' Dimethoxytrityl 3'-Methylthiomethyl thymidine (Step 1):

Dimethoxytrityl thymidine (Peninsula Labs) (0.94 g) was rotovaped from pyridine two times and then from methylene chloride/toluene one time. The resulting foam was dissolved in 75 ml dry CH$_2$Cl$_2$ and 10 ml of dry THF. 10 mg of NaI and 0.21 g of NaH (60% dispersion in oil) was added under an argon atmosphere with stirring at 20° C. After 15 min the H$_2$ bubbling stopped and the reaction was stirred for another hour. Chloromethylthiomethane (158 ul) was added and stirring under-argon continued for 16 hrs at 20° C. The reaction was quenched with 1M NaHCO$_3$, extracted and the organic layer dried with Na$_2$SO$_4$. The solution was then rotovaped to a foam and purified on a silica gel column using 5% isopropyl alcohol/CH$_2$Cl$_2$ as the eluent. Fractions were concentrated to a pure foam (yield 0.56 g) $^1$H NMR spectra was consistent with assigned structure.

Preparation of 3' Thexyldimethylsilyl thymidine:

Dimethoxytrityl thymidine (Peninsula Labs) (1 g), 20 ml of dry DMF, 193 mg of imidazole and 0.45 ml of thexyldimethylsilylchloride were combined under argon and stirred for 16 hr at 20° C. The reaction was then quenched with 2 ml MeOH and rotovaped to a foam, dissolved in EtOH (20 ml) and treated with 0.6 ml of dichloroacetic acid for 16 hr at 20° C. The reaction was quenched with 1M NaHCO$_3$ and extracted with CH$_2$Cl$_2$. The organic layer was dried with Na$_2$SO$_4$. This solution was rotovaped to a foam, dissolved in 5 ml of diethylether and precipitated into 50 ml of hexane. The ether was rotovaped off as the white precipitate became heavy and upon filtration and drying, 0.5 g of pure white foam was recovered. The $^1$H NMR spectra was consistent with the assigned structure.

Preparation of 5' OH 3' Thexyldimethylsilyl thymidine formacetal thymidine (Steps 2 and 3):

5' dimethoxytrityl 3' methylthiomethyl thymidine (78 mg) and 3' thexyldimethylsilyl thymidine (60 mg) were rotovaped from toluene and dissolved in 2 ml of dry toluene. 50 mg of activated 4A molecular sieves and Di-t-butyl pyridine (0.144 ml) were added and the reaction was stirred for 16 hr under argon. N-Bromosuccinimide (13 mg) was then added and the reaction stirred for 1 hr at 20° C. The reaction was quenched with 1M NaHCO$_3$ and extracted with CH$_2$Cl$_2$. The organic layer was dried with Na$_2$SO$_4$. The solution was rotovaped to a foam and then treated with 4 ml of 20% H$_2$O/HOAc for 2hr at 20° C. The reaction was quenched in 1M NaHCO$_3$, extracted with CH$_2$Cl$_2$, dried with Na$_2$SO$_4$ and rotovaped to a foam. The foam was purified by silica gel chromatography using 3% to 10% IsOH/CH$_2$Cl$_2$ as the eluent yielding 60 mgs of pure product after evaporation of solvent. The $^1$H NMR spectra was consistent with the assigned structure.

Preparation of 5' Dimethoxytrityl 3' OH thymidine formacetal thymidine formacetal thymidine (Step 3):

5' OH 3' thexyldimethylsilyl thymidine formacetal thymidine (55 mg) was combined with dimethoxytrityl 3' methylthiomethyl thymidine (78 mg) and rotovaped from toluene. The resulting foam was dissolved in 2 ml of toluene/CH$_2$Cl$_2$ (1/1), 50 mg of activated 4A molecular sieves and di-t-butylpyridine (0.144 ml) were added and the reaction was stirred for 16 hr under argon. N-Bromosuccinimide (21 mg) was then added and the reaction stirred for 1 hr at 20° C. The reaction was quenched with 1M NaHCO₃ and extracted with CH₂Cl₂. The organic layer was dried from Na₂SO₄. The solution was rotovaped to a foam and treated with 1 ml of tetrabutylammonium fluoride in THF for 3 hr, extracted, dried and evaporated in normal fashion. The resulting foam was purified by preparative silica gel thin layer chromatography using a 10% IsOH/CH₂Cl₂ as the eluent. The ¹H NMR was consistent with the desired structure (yield: 25 mg). A small aliquot (5 mg) was deprotected at the 5' end in normal fashion.

The resulting 5' OH 3' OH thymidine formacetal thymidine formacetal thymidine was used in further characterization. ¹H NMR of this material in d₆ DMSO was consistent with the assigned structure. An aliquot of this was persilylated and a Fast Atom Bombardment Mass Spectrum was recorded. This confirmed the desired molecular weight. Additionally the di OH material was used in the chemical and enzymatic stability studies previously mentioned.
Preparation of 5' Dimethoxytrityl 3' succinylate thymidine formacetal thymidine formacetal thymidine:

5' Dimethoxytrityl 3' OH thymidine formacetal thymidine formacetal thymidine (16 mg) was treated with 9 mg of succinic anhydride and a trace of dimethylamino pyridine in pyridine for 16 hr at 20° C. The reaction was then rotovaped and extracted with 30% BuOH/CH₂Cl₂ against H₂O. The organic layer was dried, rotovaped and purified on a silica gel column using 10% H₂O/CH₃CN as the eluent. Rotovaping yielded 15 mg of product.
Preparation of 5'-TCTCCCTCTCTTT(OCH₂O)T(OCH₂O)T-3'(SEQ. ID. NO: 3)

The 3' succinylated 5'-DMT thymidine formacetal thymidine formacetal thymidine from the previous paragraph was then bound to solid support and deprotected. Standard procedures were used to extend the oligomer to obtain the title compound.

Part B: Stability to Acid

The purified product of paragraph (A) above was treated with 20% water/formic acid at 80° C. for 1 hr, resulting in complete hydrolysis. However, when subjected to moderate acid treatment such as 1M HCl at 20° C. for 3 hrs or 20% water/acetic acid at 45° C. for 3 hrs, no hydrolysis was observed.

The title compound was also stable to snake venom phosphodiesterase under standard conditions for hydrolysis of phosphodiester bonds.

Part C: Hybridization to Complementary RNA

An RNA sequence complementary to the title compound was generated using T7 transcription Milligan, T. F., et al., *Nucleic Acids Res* (1987) 15:8783). This RNA was used to test the ability of the title compound to hybridize to its complement as compared to analogous sequences wherein the acetal linkages are replaced by phosphodiesters, phosphoramidates, or wherein the 3' terminal thymidyl nucleotides were deleted. The melting temperatures of complexes formed with the title compound and these controls were measured using 100 mM NaCl, 50 mM Tris, pH 7.5 under standard conditions as described by Summers, M. F., et al., *Nucleic Acids Res* (1986) 14:7421. The results are shown in Table 3, where "12mer" stands for the TCTCCCTCTCTT- (SEQ. ID. NO: 4) nucleotide sequence common to all of the samples. In the third oligomer, "W" represents the substituent —CH₂CH₂OMe in the amidate.

TABLE 3

|  | Tm |
|---|---|
| 12 mer-T(OCH₂O)T(OCH₂O)T | 59.0 |
| 12 mer-TTT | 59.5 |
| 12 mer-T(PONHW)T(PONHW)T | 58.5 |
| 12 mer | 56.5 |

As shown in Table 1, the three thymidines linked through formacetal linkages confer additional hybridization capability on the 12mer as compared to the 12mer alone. The additional hybridization is comparable to that conferred by extension by conventional phosphodiester linkages.

Part D: Binding to Duplex DNA

Using the footprinting method described in detail in Part C of Preparation B below, the formacetal-containing oligonucleotides of this example show ability to bind duplex DNA.

Preparation B: Preparation of 5'TCTĆ(OCH₂O)
TC* (OCH₂O)TĆ(OCH₂O)TĆ(OCH₂OTTTT-3'
(SEQ. ID. NO: 5) or 5'TCTĆ.TĆ.TĆ.TĆ.TTTT- 3'
(SEQ. ID. NO: 6), (SEQ. ID. NO: 7), (SEQ. ID.
NO: 8) and SEQ. ID. NO: 9)

Part A: Preparation of Oligomers

A series of four oligomers as shown, wherein Ć represents 5-methylcytosine and the dot between Ć and T represents a linkage varied among the series of four oligomers was synthesized. In the "phosphodiester" control oligomer, the dot represents a conventional phosphodiester linkage. In the "methylphosphonate" oligomer, the dot represents a methylphosphonate linkage. In the "methoxyethyl amidate" oligomer, the dot represents a methoxyethyl amidate linkage. In the "formacetal" oligomers of the invention, the dot represents a formacetal linkage as described herein and as shown above.

The phosphodiester oligomer was synthesized using the conventional techniques described by Froehler, B.C. et al., *Nucleic Acids Res* (1986) 14:5399. The remaining three oligomers were synthesized using this method, but with the incorporation of the appropriate dimer synthon. The methylphosphonate and the methoxyethyl amidate dimer synthons were constructed using 5'-DMT-N-benzoyl-5-methyldeoxycytidine and 3-t-butyldimethylsilyl thymidine as described, respectively, by Miller, P.S. et al., *Biochemistry* (1986) 25:5092, and by Froehler, B.C., *Tet Lett* (1986) 27:5575. The formacetal dimer synthon was prepared as described hereinabove and as reported by Mateucci, M. C. et al., *Tet Lett* (1990) 31:2385, cited above. The oligos resulting from the synthesis were deblocked with concentrated ammonia for 16 hours at 20° C. and gel purified using conventional techniques.

Part B: Hybridization to RNA Complement

The complementary RNA for use as a test compound was synthesized by T7 polymerase reaction on the appropriate primer template as described by Milligan, J. F. et al., *Nucleic Acids Res* (1987) 15:8783. Appropriate complementary DNA oligomers were also constructed.

The hybridization was tested using thermal denaturation comparisons in buffer containing salts designed to mimic intracellular salt composition and concentration—i.e., 140 mM KCl, 10 mM NaCl, 5 mM $NaH_2PO_4$, 5 mM $MgCl_2$, pH 7. UV absorption was measured in the temperature range 20° C–80° C., and all oligomers gave monophasic transitions. $T_m$ values were assigned by finding the temperature at which the slope of the curve was maximum.

These results are shown in Table 4.

TABLE 4

| | $T_m$ | |
|---|---|---|
| Oligomer | ssRNA | ssDNA |
| Phosphodiester | 60.0° C. | 49.5° C. |
| Methyl Phosphonate | 50.5 | |
| Methoxyethyl Amidate | 47.5 | 38.5 |
| Formacetal | 59.0 | 39.0 |

As shown in the table, the $T_m$ of the formacetal oligomer in comparison to the phosphodiester is roughly equal for single-stranded RNA. On the other hand, the $T_m$ values for the alternate analogs methylphosphonate and methoxyethyl amidate oligomers was appreciably lower. Thus, despite the advantages conferred by the formacetal linkage—for example, enhanced ability to cross cell membranes and enhanced nuclease resistance, no decrease in the hybridization power to single-stranded RNA was detected.

Part C: Binding to Duplex DNA

The "footprint" assay described by Cooney, M. et al., Science (1988) 241:456, was used. The assay is based on the ability of the oligomer bound to duplex to protect the duplex from digestion with DNAse I. Various concentrations of the test oligomer ranging from 0.1–10 μM were incubated with a $p^{32}$ radiolabeled restriction fragment bearing the target sequence at 1 nM concentration in 10 mM NaCl, 140 mM KCl, 1 mM $MgCl_2$, 1 mM spermine and 20 mM MOPS buffer at pH 7 for 2 hours. The target sequence for the set of oligomers prepared in Part A of this example was

—AGAGAGAGAGAAAA—          (SEQ. ID. NO: 10)

—TCTCTCTCTCTTTT—          (SEQ. ID. NO: 11)

DNAse I was added to permit limited digestion, the samples were then denatured and subjected to polyacrylamide gel electrophoresis which separates the DNA fragments based on size.

An outline of the principle of the footprint assay and idealized results are shown in FIG. 1. As shown in FIG. 1, the labeled duplex, when treated with DNAse, should yield lengths of oligomer corresponding to cleavage at each diester linkage, thus obtaining the series of bands shown on the left in the idealized gel. On the other hand, when the duplex is protected by binding to the oligomer, the series of lengths represented by cleavage at the diester linkages in the region protected by binding to the oligomer is missing from the gel. This "footprint" indicates the region of protection. The results are semiquantitatively estimated by observing either the complete absence of, or only weak appearance of, bands in the region of the footprint.

The formacetal oligomer and the phosphodiester oligomer showed partial protection of the target sequence at 0.1 μM and more than 90% protection at 1 μM concentration of the oligomer. On the other hand, the methoxyethyl phosphoramidate and the methylphosphonate showed only partial protection at 1 μM and >90% protection at 10 μM. Thus, these oligomers appeared to have markedly less affinity for the duplex than the formacetal oligomer.

EXAMPLE 1

Preparation of 5'DMTO-T*—$OCH_2O$-T*—OH-3'

A mixture of 5'-DMTO-T*—$OCH_2SCH_3$ 3', prepared as in Example 1 (0.9 g, 1.5 mmol), 5'-HO-T*-$OSiMe_2$Tx, also prepared as in Example 1 (0.8 g, 2.2 mmol), 2,6-diethylpyridine (1 g, 7.4 mmol) and molecular sieves (4 Å, 2 g) in dry benzene (60 ml) was stirred at room temperature (RT) for 1 hr. This was followed by addition of 1.5 ml of a 1.0M solution of bromine in benzene (1.5 mmol). The resulting solution was then stirred at RT for 2 hr and washed with saturated aqueous $NaHCO_3$ solution.

The organic solution was separated, dried ($Na_2SO_4$), evaporated to dryness, then redissolved in dry THF (10 ml) and treated with 4 ml of a 1.0M solution of tetrabutylammonium fluoride in THF at RT for 30 min. The reaction was concentrated and then partitioned between methylene chloride and saturated aqueous $NaHCO_3$ solution twice, dried, and evaporated to dryness. The residue was purified by flash column chromatography (silica gel) on a 25 mm column using one column volume of 1% TEA/$CH_2CH_2$, then two column volumes of 1% TEA/2.5% $CH_3OH$, and then one column volume of 1% TEA/5% $CH_3OH/CH_2Cl_2$. This afforded 0.84 g of product, 5' DMTO-T*—$OCH_2O$-T —OH 3', as a colorless foam (71% yield).

EXAMPLE 2

Preparation and Characterization of 5' HO-T*—$SCH_2O$-T*—OH 3'

Part A: Preparation of the Dimer

To prepare 5'-methylthiomethyl-3'-t-butyldimethyl silyl thymidine, to a THF solution (15 ml) of 3'-t-butyl dimethyl silyl thymidine (1.8 g, 5 mmol) was added sodium hydride (0.24 g, 10 mmol). The solution was stirred at RT for 30 min; then sodium iodide (0.74 g, 5 mmol) and chloromethyl methyl sulfide (0.53 g, 5.5 mmol) were added. After 1 hr reaction at RT, the reaction mixture was diluted with methylene chloride (100 ml), then washed with saturated $NaHCO_3$ aqueous solution twice. The organic phase was isolated, dried over $Na_2SO_4$, concentrated to dryness, and purified by flash column chromatography on silica gel, affording 0.68 g of the 5' $MeSCH_2O$-T-O* $SiMe_2tBu$ 3' (32% yield).

The 5' $MeSCH_2O$-T-O* $SiMe_2tBu$ 3' from the preceding paragraph (0.55 g, 2.17 mmol), 2,6-diethylpyridine (1.46 g, 11 mmol), and molecular sieves (4 Å, 5 g) in dry benzene (40 ml) were stirred at RT for 30 min. This was followed by addition of 2.2 ml of a 1M solution of bromine in benzene (2.2 mmol). The resulting solution was stirred at RT for 30 min followed by addition of 5'-dimethoxytrityl-3'-thiothymidine (1.35 mmol) in benzene (20 ml). The 3'-thio sugar is prepared as set forth in Horwitz, P., et al., *J Org Chem* (1964) 2.9:2076, (Cosstick, R., et al., *Chem Soc Chem Commun* (1988) 992).

After 2 hr reaction at RT, the molecular sieves were filtered off, washed with benzene, and the combined benzene solution was washed with saturated $NaHCO_3$ aqueous solution, dried ($Na_2SO_4$), and concentrated to dryness. The residue was redissolved in THF (3 ml) and treated with 3 ml of a 1M THF solution of tetrabutylammonium fluoride at RT for 1 hr. The reaction mixture was concentrated, then partitioned between methylene chloride and saturated NaHCO$_3$ aqueous solution twice. The organic phase was separated, dried, and concentrated. The residue was purified by flash column chromatography on silica gel, affording 0.24 g of 5'DMTO-T*—SCH$_2$O-T*—OH 3' dimer (yield 22%).

Part B: Characterization of Oligonucleotides Containing —SCH$_2$O— linkages

The TT 3'-thioformacetal thymidine dimer of the preceding paragraph was incorporated as a dimer block into the deoxyoligonucleotide sequence 5'TTT-tf-TĆTT-tf-TĆTĆĆT-tf-TT-tf-TTQ    (SEQ. ID. NO: 12)

wherein tf is the 3' thioformacetal linkage, all other linkages are phosphorodiester, Ć is 5-methyl deoxycytidine and Q is an anthraquinone pseudonucleoside as described in U.S. Ser. No. 482,941, filed 20 Feb. 1990, and incorporated herein by reference. The ability of this oligomer to hybridize to RNA was assessed by thermal denaturation of the duplex of the oligomer and the RNA sequence 3' UAAAAGAAAGGAG-GAAAAAU(SEQ. ID. NO: 13). Tm values for this denaturation were compared to those for identical sequences wherein either formacetal per se (—OCH$_2$O—) or phosphodiester was present in the "tf" position.

The Tm for the control phosphorodiester was 69° C.; the Tm for the formacetal was 67° C., and that for the 3' thioformacetal was 71° C.; thus, the 3' thioformacetal linkage hybridizes more strongly to RNA than either phosphodiester or the formacetal.

To assess triplex formation, thermal denaturation of the above oligomers and the duplex target 5' AAAAGAAAG-GAGGAAAAA(SEQ. ID. NO: 14) was measured.

The Tm values for the triplex transitions at pH 6.2, (140 mM KCl, 5 mM NaCl, 5 mM MgCl$_2$, 5 mM Na phosphate) are: phosphodiester, 47.7° C.; formacetal, 44.1° C., 3' thioformacetal, 50.4° C. Thus, the 3' thioformacetal linkage confers stronger triplex formation than either the phosphorodiester or formacetal linkages.

Triplex formation was also assessed by DNAse I footprinting at pH 7.2, 20 mM MOPS, 140 mM KCl, 10 mM NaCl, 1 mM MgCl$_2$, 1 mM spermine. The 3' thioformacetal and exclusively phosphodiester oligomer were able to protect the target region from nuclease partially at 10 μM while the formacetal showed little protection at 100 μM.

EXAMPLE 3

Preparation of 5' HO-T*—OCF$_2$O-T*—OH

5' Pivaloyl-3'HO thymidine (1 g) and thiocarbonylimidazole (1.2 g) were combined in 8 ml of dry acetonitrile (CA) and heated under inert gas at 60° C. for 16 hr. TLC analysis showed complete conversion to a faster spot (5% isopropanol/CH$_2$Cl$_2$). The reaction was cooled, diluted with CH$_2$Cl$_2$ and washed with 1M HCl and then sodium phosphate buffer (pH 9). The organic layer was rotovaped to dryness, dissolved in dry ACN and rerotovaped; this was repeated three times.

This thiocarbonylimidazole product (746 mg) was combined with an excess of 5' HO-3'-isobutyl carbonylthymidine (810 mg) and 120 mg of tetrazole in 7 ml of dry ACN and 7 ml ethanol-free CHCl$_3$, heated under inert gas in a sealed vessel at 80° C. for 48 hr. The reaction was diluted with CH$_2$Cl$_2$, washed with phosphate buffer, concentrated and purified by flash column chromatography to yield one pure fraction of 145 mg and less pure fractions of 450 mg.

The pure material was then dried by coevaporation from dry ACN and desulfurized and fluorinated by treatment with 60 μl of diethylamino trifluoro sulfur (DAST) in 1 ml of dry ACN under inert gas at 40° C. for 16 hrs. The product comigrates with the starting material on TLC (5% Isopropanol/CH$_2$Cl$_2$). The reaction was diluted with CH$_2$CL$_2$ and washed with phosphate buffer, evaporated and purified on a preparative TLC plate eluting with 5% IsOH/CH$_2$Cl$_2$.

The recovered material was deprotected with 0.15M sodium hydroxide in dioxane/H$_2$O (1/1) at 20° C. for 16 hrs. The reaction was then neutralized with acetic acid, concentrated and purified by prep TLC eluting with H$_2$O/ACN (1/9). The product, 5' HO-T*—OCF$_2$O-T*—OH 3' had an Rf on silica TLC, eluting with H$_2$O/ACN (1/9), slightly faster than thymidine.

EXAMPLE 4

Preparation of a T-T Tetrahydropyran Ketal

5'-HO-3'-benzoyl thymidine was reacted with 5,6-dihydro-4-methoxy-2H-pyran producing 5'-(4-methoxy tetrahydro pyrano-4-yl) thymidine as described by Reese, C. B. et al., Tetrahedron (1970) 26:1023–1030. A mixture of 5'-pivaloyl thymidine 0.23 grams (0.5 mmol) and of the 5'-(4-methoxytetrahydropyran-4-yl)-3'-benzoyl thymidine (0.32 grams, 1 mmol) was rotovaped from dry acetonitrile (ACN) three times to render them anhydrous. This gum was then dissolved in 2 ml of dry ethanol-free chloroform (CHCl$_3$) and 1 gram of freshly activated 4A molecular sieves was added. The reaction was agitated on a shaker at 20° C. for 16 hrs under inert gas. 10 mmol of p-toluenesulfonic acid (TSA) (previously dried by evaporation three times from dry ACN) was added in 0.2 ml of dry CHCl$_3$ and the reaction was agitated for 2 hrs at 50° C. under inert gas. The reaction was cooled to 20° C. and quenched with 0.5 ml of triethylamine (TEA).

The workup consisted of dilution with CH$_2$Cl$_2$ and extraction with 0.5M sodium phosphate pH 9, rotovaping to dryness, dissolving in toluene and rerotovaping to remove the residual TEA and H$_2$O. This mixture was purified by preparative thin layer chromatography, eluting with 5% isopropanol in CH$_2$Cl$_2$.

EXAMPLE 5

Synthesis of Oligonucleotides with 5'-SCH$_2$O-3' Internucleoside Linkages

A. Preparation of 5'DMTO-T*—SCH$_2$O-T*—OH3'

Anhydrous HCl was bubbled for 10 min into a solution of 3'-dodecoyl thymidine (4.41 g, 10.4 mmol) and paraformaldehyde (467 mg, 15.6 mmol) in methylene chloride (100 mL) at 0° C., and the solution was held at 4° C. for 48 h. The solution was dried over Na$_2$SO$_4$, and solvent removed in the rotary evaporator to afford the 5'-chloromethyl ether of the ester starting material. This chloromethyl ether was dissolved in methylene chloride (25 mL) and added dropwise to a 0° C. solution of 5'-DMT-3'-thiothymidine (7.01 g, 12.5 mmoles) and diisopropylethylamine (DIPEA, 3.23 g, 26 mmol) in methylene chloride (100 mL). The organic layer was separated, dried over Na$_2$SO$_4$, concentrated on the rotary evaporator, and purified by silica gel chromatography to deliver the product 5'DMT-O-T*—SCH$_2$O-T*—OOC $(CH_2)_{10}CH_3$3' (2.0 g, 20%). (The notation corresponds to that described for reaction schemes 5–7.)

The above product (1.0 g, 2.0 mmol) was treated with sodium methoxide (1.08 g, 20.0 mmol) in methanol (20 mL) for 1 hr. The reaction was quenched with acetic acid (1.145 mL), and concentrated. The crude product was extracted with methylene chloride, dried ($Na_2SO_4$) and purified by silica gel chromatography to deliver the 3'-deprotected dimer 5'-DMT—T*—$SCH_2O$—T*—OH (550 mg, 34%). This compound was converted to the phosphonate as described above.

B. Preparation of 5'T*—$SCH_2O$—Ć*—OH3'

In a solution of 3'-phenoxyacetyl-N-4-benzoyl-5-methyl-cytidine (1.70 g, 3.55 mmol) and paraformaldehyde (159 mg, 5.32 mmol) in methylene chloride (75 mL) at 0° C. was bubbled anhydrous HCl for 10 min, and the solution was held at 4° C. for 48 hr. The solution was dried over $Na_2SO_4$, and the solvent was removed on the rotary evaporator to deliver the chloromethyl ether of the ester starting material, 5'$ClCH_2O$-Ć*—$OOCCH_2OPh$3'.

This compound was dissolved in methylene chloride (15 mL) and added dropwise to a solution of 5'-DMT-3'-thio-thymidine (1.43 g, 2.56 mmol) and DIPEA (0.826 g, 6.40 mmol) in methylene chloride (75 mL). After stirring for 3 hr, the reaction was quenched with aqueous saturated sodium bicarbonate (50 mL) and the organic layer was separated, dried over $Na_2SO_4$, concentrated on the rotary evaporator, and purified by silica gel chromatography to deliver the product 5'-DMT—T*—$SCH_2O$—Ć*—$OOCCH_2Ph$-3' (1.35 g, 50%).

The protected 5'-DMT—T*—$SCH_2O$—Ć*—$OOCCH_2OPh$-3' was selectively deblocked at the 3' position by treatment with ammonium hydroxide (10 mL) in dioxane (25 mL) for 1 hr. The solution was concentrated. Ethanol (50 mL) was added, and the solution was concentrated. Purification by silica gel chromatography delivered the deprotected product above (230 mg, 75%), which was converted to the phosphonate as described above.

C. Incorporation of the Dimer Synthons Into Oligonucleotides

The dimer synthons prepared in paragraphs A and B hereinabove were incorporated into oligonucleotides using standard solid-phase synthesis techniques. In addition to these synthons, corresponding dimers prepared as set forth above having the internucleoside linkage —$OCH_2O$— were prepared as controls.

D. Binding Affinity of Oligomers Containing Formacetal (—$OCH_2O$—) and Thioformacetal (5'-$SCH_2O$-3') Linkages The —$OCH_2O$— and 3'-formacetal 5'-$SCH_2O$-3' neutral linkages, represented as T$^†$T and T$^†$Ć (where Ć is 5-methyl-C), dimer synthons incorporated into the sequence T$^†$ĆT$^†$ĆT$^†$ĆT$^c$T$^c$T$^c$ T$^†$T$^†$T T (SEQ. ID. NO: 15) were tested for binding affinity using melting point (Tm) as a criterion.

The Tms were measured in three different modes: triplex (dsDNA) at pH 7.0 with 140 mM KCl, 5 mM $Na_2HPO_4$ and 1 mM $MgCl_2$; single-stranded RNA at pH 6.6 with 140 mM KCl, 5 mM $Na_2HPO_4$ and 1 mM $MgCl_2$; and single-stranded DNA at pH 6.6 with 140 mM KCl, 5 mM $Na_2HPO_4$ and 1 mM $MgCl_2$. The results are shown in Table 5.

TABLE 5

| | T † C T † C T † C T † C T † C T † T T † T T (SEQ ID NO:16, (SEQ ID NO:17), and (SEQ ID NO:18) | | |
|---|---|---|---|
| | 7.0 | ssRNA | ssDNA |
| All † = Diester | ds DNA 31.8 | 62.0 | 55.0 |
| All † = —$OCH_2O$— | 32.0(+0.2) | 57.5(−4.5) | 50.0(−5.0) |
| All † = —$SCH_2O$— | 43.9(+11.9) | 67.5(+5.5) | 63.0(+8.0) |

In the triplex mode, the —$OCH_2$— linked oligomer melted at a similar temperature to the diester control a pH 7.0, while the —$SCH_2O$— linked oligomer melted 11.9 degrees higher at pH 7.0.

Against ssRNA and ssDNA the —$OCH_2$— linked oligomer melted at 4.5 and 5.0 degrees lower than the control diester, while the —$SCH_2O$— linked oligomer melted at 5.5 and 8.0 degrees higher than control against ssRNA and ssDNA respectively.

In the footprint assay described above in Preparation B, part C, with 1 hr incubation with duplex target at 37° C. and pH 7.2 buffer of 20 mM MOPS, 140 mM KCl, mM NaCl, 1 mM $MgCl_2$, and 1 mM spermine, the diester control showed complete protection at 10 μM concentration and partial protection at 1 μM. The —$OCH_2O$— linked oligomer showed no footprint at 1 or 10 μM. The —$SCH_2O$— linked oligomer showed complete protection at 10 μM concentration and partial protection at 1 μM.

In conclusion, the 5'-$SCH_2$—O-3'-containing oligomer is superior in binding to diester in all Tm assays and equivalent to diester in the triplex footprint assay.

---

We claim:

1. A method to link a first nucleoside or oligonucleotide and a second nucleoside or nucleotide 3'–5' through a linkage having the formula —OCH$_2$O—, which method comprises (a.) treating a first 5' protected nucleoside or nucleotide derivatized at the 3' position with a functional group of the formula —OCH$_2$SCH$_3$ and a second nucleoside or nucleotide protected at the 3' position with bromine in the presence of 2,6-diethylpyridine and molecular sieves, (b.) followed by treatment with tetrabutylammonium fluoride in a tetrahydrofuran (THF) solvent to obtain said first nucleoside or oligonucleotide and second nucleoside or nucleotide coupled 3'–5' through the linkage of the formula —OCH$_2$O.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(4, "")
        ( D ) OTHER INFORMATION: /note="This position is (SCX20)."

( i x ) FEATURE:
    ( A ) NAME/KEY: misc_difference
    ( B ) LOCATION: replace(9, "")
    ( D ) OTHER INFORMATION: /note="This position is (SCX2O)."

( x i ) SEQUENCE DESCRIPTION: SEQ ID NO:1:

ATGNGTCANA GG                                                                                                     12

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ATGGTCAAGG                                                                                                      10

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(14, "")
        ( D ) OTHER INFORMATION: /note="This position is (OCH2O)."

( i x ) FEATURE:
        ( A ) NAME/KEY: misc_difference
        ( B ) LOCATION: replace(16, "")
        ( D ) OTHER INFORMATION: /note="This position is (OCH2O)."

( x i ) SEQUENCE DESCRIPTION: SEQ ID NO:3:

TCTCCCTCTC TTTNTNT                                                                      17

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TCTCCCTCTC TT                                                                              12

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(4, "")
        ( D ) OTHER INFORMATION: /note="This position is
            5- methylcytosine."

( i x ) FEATURE:
        ( A ) NAME/KEY: misc_difference
        ( B ) LOCATION: replace(5, "")
        ( D ) OTHER INFORMATION: /note="This position is (OCH2O)."

( i x ) FEATURE:
        ( A ) NAME/KEY: misc_difference (B) LOCATION: replace(8, "")
(D) OTHER INFORMATION: /note="This position is (OCH2O)."

(ix) FEATURE:
(A) NAME/KEY: misc_difference
(B) LOCATION: replace(10, "")
(D) OTHER INFORMATION: /note="This position is
5- methylcytosine."

(ix) FEATURE:
(A) NAME/KEY: misc_difference
(B) LOCATION: replace(11, "")
(D) OTHER INFORMATION: /note="This position is (OCH2O)."

(ix) FEATURE:
(A) NAME/KEY: misc_difference
(B) LOCATION: replace(13, "")
(D) OTHER INFORMATION: /note="This position is
5- methylcytosine."

(ix) FEATURE:
(A) NAME/KEY: misc_difference
(B) LOCATION: replace(14, "")
(D) OTHER INFORMATION: /note="This position is (OCH2O)."

(xi) SEQUENCE DESCRIPTION: SEQ ID NO:5:

TCTCNTCNTC NTCNTTTT 18

(2) INFORMATION FOR SEQ ID NO:6:

(i) SEQUENCE CHARACTERISTICS:
(A) LENGTH: 14 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(4, "")
(D) OTHER INFORMATION: /note="This position is
5- methylcytosine."

(ix) FEATURE:
(A) NAME/KEY: misc_difference
(B) LOCATION: replace(4..5, "")
(D) OTHER INFORMATION: /note="This position indicates a
phosphodiester linkage."

(ix) FEATURE:
(A) NAME/KEY: misc_difference
(B) LOCATION: replace(6, "")
(D) OTHER INFORMATION: /note="This position is
5- methylcytosine."

(ix) FEATURE:
(A) NAME/KEY: misc_difference
(B) LOCATION: replace(6..7, "")
(D) OTHER INFORMATION: /note="This position indicates a
phosphodiester linkage."

(ix) FEATURE:
(A) NAME/KEY: misc_difference
(B) LOCATION: replace(8, "")
(D) OTHER INFORMATION: /note="This position is
5- methylcytosine."

(ix) FEATURE:
(A) NAME/KEY: misc_difference
(B) LOCATION: replace(8..9, "")
(D) OTHER INFORMATION: /note="This position indicates a
phosphodiester linkage."

(ix) FEATURE:
(A) NAME/KEY: misc_difference
(B) LOCATION: replace(10, "")
(D) OTHER INFORMATION: /note="This position is
5- methylcytosine."

( i x ) FEATURE:
  ( A ) NAME/KEY: misc_difference
  ( B ) LOCATION: replace(10..11, "")
  ( D ) OTHER INFORMATION: /note="This position indicates a phosphodiester linkage."

( x i ) SEQUENCE DESCRIPTION: SEQ ID NO:6:

TCTCTCTCTC TTTT 14

( 2 ) INFORMATION FOR SEQ ID NO:7:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(4, "")
    ( D ) OTHER INFORMATION: /note="This position is 5- methylcytosine."

( i x ) FEATURE:
    ( A ) NAME/KEY: misc_difference
    ( B ) LOCATION: replace(4..5, "")
    ( D ) OTHER INFORMATION: /note="This position indicates a methylphosphonate linkage."

( i x ) FEATURE:
    ( A ) NAME/KEY: misc_difference
    ( B ) LOCATION: replace(6, "")
    ( D ) OTHER INFORMATION: /note="This position is 5- methylcytosine."

( i x ) FEATURE:
    ( A ) NAME/KEY: misc_difference
    ( B ) LOCATION: replace(6..7, "")
    ( D ) OTHER INFORMATION: /note="This position indicates a methylphosphonate linkage."

( i x ) FEATURE:
    ( A ) NAME/KEY: misc_difference
    ( B ) LOCATION: replace(8, "")
    ( D ) OTHER INFORMATION: /note="This position is 5- methylcytosine."

( i x ) FEATURE:
    ( A ) NAME/KEY: misc_difference
    ( B ) LOCATION: replace(8..9, "")
    ( D ) OTHER INFORMATION: /note="This position indicates a methylphosphonate linkage."

( i x ) FEATURE:
    ( A ) NAME/KEY: misc_difference
    ( B ) LOCATION: replace(10, "")
    ( D ) OTHER INFORMATION: /note="This position is 5- methylcytosine."

( x i ) SEQUENCE DESCRIPTION: SEQ ID NO:7:

TCTCTCTCTC TTTT 14

( 2 ) INFORMATION FOR SEQ ID NO:8:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(4, "")
    ( D ) OTHER INFORMATION: /note="This position is 5- methylcytosine."

( i x ) FEATURE:
    ( A ) NAME/KEY: misc_difference
    ( B ) LOCATION: replace(4..5, "")
    ( D ) OTHER INFORMATION: /note="This position indicates a
        methoxyethyl amidate linkage."

( i x ) FEATURE:
    ( A ) NAME/KEY: misc_difference
    ( B ) LOCATION: replace(6, "")
    ( D ) OTHER INFORMATION: /note="This position is
        5- methylcytosine."

( i x ) FEATURE:
    ( A ) NAME/KEY: misc_difference
    ( B ) LOCATION: replace(6..7, "")
    ( D ) OTHER INFORMATION: /note="This position indicates a
        methoxyethyl amidate linkage."

( i x ) FEATURE:
    ( A ) NAME/KEY: misc_difference
    ( B ) LOCATION: replace(8, "")
    ( D ) OTHER INFORMATION: /note="This position is
        5- methylcytosine."

( i x ) FEATURE:
    ( A ) NAME/KEY: misc_difference
    ( B ) LOCATION: replace(8..9, "")
    ( D ) OTHER INFORMATION: /note="This position indicates a
        methoxyethyl amidate linkage."

( i x ) FEATURE:
    ( A ) NAME/KEY: misc_difference
    ( B ) LOCATION: replace(10, "")
    ( D ) OTHER INFORMATION: /note="This position is
        5- methylcytosine."

( i x ) FEATURE:
    ( A ) NAME/KEY: misc_difference
    ( B ) LOCATION: replace(10..11, "")
    ( D ) OTHER INFORMATION: /note="This position indicates a
        methoxyethyl amidate linkage."

( x i ) SEQUENCE DESCRIPTION: SEQ ID NO:8:

TCTCTCTCTC TTTT                                                  14

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(4, "")
        ( D ) OTHER INFORMATION: /note="This position is
            5- methylcytosine."

( i x ) FEATURE:
        ( A ) NAME/KEY: misc_difference
        ( B ) LOCATION: replace(4..5, "")
        ( D ) OTHER INFORMATION: /note="This position indicates a
            formacetal linkage."

( i x ) FEATURE:
        ( A ) NAME/KEY: misc_difference
        ( B ) LOCATION: replace(6, "")
        ( D ) OTHER INFORMATION: /note="This position is
            5- methylcytosine."

( i x ) FEATURE:
        ( A ) NAME/KEY: misc_difference
        ( B ) LOCATION: replace(6..7, "")
        ( D ) OTHER INFORMATION: /note="This position indicates a
            formacetal linkage."

( i x ) FEATURE:

( A ) NAME/KEY: misc_difference
              ( B ) LOCATION: replace(8, "")
              ( D ) OTHER INFORMATION: /note="This position is
                    5- methylcytosine."

( i x ) FEATURE:
              ( A ) NAME/KEY: misc_difference
              ( B ) LOCATION: replace(8..9, "")
              ( D ) OTHER INFORMATION: /note="This position indicates a
                    formacetal linkage."

( i x ) FEATURE:
              ( A ) NAME/KEY: misc_difference
              ( B ) LOCATION: replace(10, "")
              ( D ) OTHER INFORMATION: /note="This position is
                    5- methylcytosine."

( i x ) FEATURE:
              ( A ) NAME/KEY: misc_difference
              ( B ) LOCATION: replace(10..11, "")
              ( D ) OTHER INFORMATION: /note="This position indicates a
                    formacetal linkage."

( x i ) SEQUENCE DESCRIPTION: SEQ ID NO:9:

TCTCTCTCTC TTTT                                                                                         1 4

( 2 ) INFORMATION FOR SEQ ID NO:10:

( i ) SEQUENCE CHARACTERISTICS:
              ( A ) LENGTH: 14 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:10:

AGAGAGAGAG AAAA                                                                                         1 4

( 2 ) INFORMATION FOR SEQ ID NO:11:

( i ) SEQUENCE CHARACTERISTICS:
              ( A ) LENGTH: 14 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:11:

TCTCTCTCTC TTTT                                                                                         1 4

( 2 ) INFORMATION FOR SEQ ID NO:12:

( i ) SEQUENCE CHARACTERISTICS:
              ( A ) LENGTH: 18 base pairs
              ( B ) TYPE: nucleic acid
              ( C ) STRANDEDNESS: single
              ( D ) TOPOLOGY: linear ( i x ) FEATURE:
              ( A ) NAME/KEY: misc_difference
              ( B ) LOCATION: replace(3..4, "")
              ( D ) OTHER INFORMATION: /note="This position indicates a
                    formacetal linker group."

( i x ) FEATURE:
              ( A ) NAME/KEY: misc_difference
              ( B ) LOCATION: replace(5, "")
              ( D ) OTHER INFORMATION: /note="This position is 5-methyl
                    deoxycytidine."

( i x ) FEATURE:
              ( A ) NAME/KEY: misc_difference
              ( B ) LOCATION: replace(7..8, "")
              ( D ) OTHER INFORMATION: /note="This position indicates a
                    formacetal linker group."

( i x ) FEATURE:
    ( A ) NAME/KEY: misc_difference
    ( B ) LOCATION: replace(9, "")
    ( D ) OTHER INFORMATION: /note="This position is 5-methyl deoxycytidine."

( i x ) FEATURE:
    ( A ) NAME/KEY: misc_difference
    ( B ) LOCATION: replace(11, "")
    ( D ) OTHER INFORMATION: /note="This position is 5-methyl deoxycytidine."

( i x ) FEATURE:
    ( A ) NAME/KEY: misc_difference
    ( B ) LOCATION: replace(12, "")
    ( D ) OTHER INFORMATION: /note="This position is 5-methyl deoxycytidine."

( i x ) FEATURE:
    ( A ) NAME/KEY: misc_difference
    ( B ) LOCATION: replace(13..14, "")
    ( D ) OTHER INFORMATION: /note="This position indicates a formacetal linkage."

( i x ) FEATURE:
    ( A ) NAME/KEY: misc_difference
    ( B ) LOCATION: replace(15..16, "")
    ( D ) OTHER INFORMATION: /note="This position indicates a formacetal linker."

( i x ) FEATURE:
    ( A ) NAME/KEY: misc_difference
    ( B ) LOCATION: replace(18, "")
    ( D ) OTHER INFORMATION: /note="This position is an anthraquinone pseudonucleoside."

( x i ) SEQUENCE DESCRIPTION: SEQ ID NO:12:

TTTTCTTTCT CCTTTTTN     18

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

UAAAGAAAG GAGGAAAAAU     20

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AAAAGAAAGG AGGAAAAA     18

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1..2, "")
        ( D ) OTHER INFORMATION: /note="This position indicates 3'- formacetal 5'-SCH2O-3'neutral linkage."

( i x ) FEATURE:
  ( A ) NAME/KEY: misc_difference
  ( B ) LOCATION: replace(2, "")
  ( D ) OTHER INFORMATION: /note="This position is
    5-methyl-C'."

( i x ) FEATURE:
  ( A ) NAME/KEY: misc_difference
  ( B ) LOCATION: replace(3..4, "")
  ( D ) OTHER INFORMATION: /note="This position indicates
    3'- formacetal 5'-SCH2O-3'neutral linkage."

( i x ) FEATURE:
  ( A ) NAME/KEY: misc_difference
  ( B ) LOCATION: replace(4, "")
  ( D ) OTHER INFORMATION: /note="This position is
    5-methyl-C'."

( i x ) FEATURE:
  ( A ) NAME/KEY: misc_difference
  ( B ) LOCATION: replace(5..6, "")
  ( D ) OTHER INFORMATION: /note="This position indicates
    3'- formacetal 5'-SCH2O-3'neutral linkage."

( i x ) FEATURE:
  ( A ) NAME/KEY: misc_difference
  ( B ) LOCATION: replace(6, "")
  ( D ) OTHER INFORMATION: /note="This position is
    5-methyl-C'."

( i x ) FEATURE:
  ( A ) NAME/KEY: misc_difference
  ( B ) LOCATION: replace(7..8, "")
  ( D ) OTHER INFORMATION: /note="This position indicates
    3'- formacetal 5'-SCH2O-3'neutral linkage."

( i x ) FEATURE:
  ( A ) NAME/KEY: misc_difference
  ( B ) LOCATION: replace(8, "")
  ( D ) OTHER INFORMATION: /note="This position is
    5-methyl-C'."

( i x ) FEATURE:
  ( A ) NAME/KEY: misc_difference
  ( B ) LOCATION: replace(9..10, "")
  ( D ) OTHER INFORMATION: /note="This position indicates
    3'- formacetal 5'-SCH2O-3'neutral linkage."

( i x ) FEATURE:
  ( A ) NAME/KEY: misc_difference
  ( B ) LOCATION: replace(10, "")
  ( D ) OTHER INFORMATION: /note="This position is
    5-methyl-C'."

( i x ) FEATURE:
  ( A ) NAME/KEY: misc_difference
  ( B ) LOCATION: replace(11..12, "")
  ( D ) OTHER INFORMATION: /note="This position indicates
    - OCH2O- neutral linkage."

( i x ) FEATURE:
  ( A ) NAME/KEY: misc_difference
  ( B ) LOCATION: replace(13..14, "")
  ( D ) OTHER INFORMATION: /note="This position indicates
    - OCH2O- neutral linkage."

( x i ) SEQUENCE DESCRIPTION: SEQ ID NO:15:

TCTCTCTCTC TTTTT                                                                15

( 2 ) INFORMATION FOR SEQ ID NO:16:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i x ) FEATURE:
    ( A ) NAME/KEY: misc_difference
    ( B ) LOCATION: replace(1..2, "")
    ( D ) OTHER INFORMATION: /note="This position indicates a diester linkage."

( i x ) FEATURE:
    ( A ) NAME/KEY: misc_difference
    ( B ) LOCATION: replace(3..4, "")
    ( D ) OTHER INFORMATION: /note="This position indicates a diester linkage."

( i x ) FEATURE:
    ( A ) NAME/KEY: misc_difference
    ( B ) LOCATION: replace(5..6, "")
    ( D ) OTHER INFORMATION: /note="This position indicates a diester linkage."

( i x ) FEATURE:
    ( A ) NAME/KEY: misc_difference
    ( B ) LOCATION: replace(7..8, "")
    ( D ) OTHER INFORMATION: /note="This position indicates a diester linkage."

( i x ) FEATURE:
    ( A ) NAME/KEY: misc_difference
    ( B ) LOCATION: replace(9..10, "")
    ( D ) OTHER INFORMATION: /note="This position indicates a diester linkage."

( i x ) FEATURE:
    ( A ) NAME/KEY: misc_difference
    ( B ) LOCATION: replace(11..12, "")
    ( D ) OTHER INFORMATION: /note="This position indicates a diester linkage."

( i x ) FEATURE:
    ( A ) NAME/KEY: misc_difference
    ( B ) LOCATION: replace(13..14, "")
    ( D ) OTHER INFORMATION: /note="This position indicates a diester linkage."

( x i ) SEQUENCE DESCRIPTION: SEQ ID NO:16:

TCTCTCTCTC TTTTT    15

( 2 ) INFORMATION FOR SEQ ID NO:17:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(1..2, "")
        ( D ) OTHER INFORMATION: /note="This position indicates a formacetal linkage."

( i x ) FEATURE:
        ( A ) NAME/KEY: misc_difference
        ( B ) LOCATION: replace(3..4, "")
        ( D ) OTHER INFORMATION: /note="This position indicates a formacetal linkage."

( i x ) FEATURE:
        ( A ) NAME/KEY: misc_difference
        ( B ) LOCATION: replace(5..6, "")
        ( D ) OTHER INFORMATION: /note="This position indicates a formacetal linkage."

( i x ) FEATURE:
        ( A ) NAME/KEY: misc_difference
        ( B ) LOCATION: replace(7..8, "")
        ( D ) OTHER INFORMATION: /note="This position indicates a formacetal linkage."

( i x ) FEATURE:

( A ) NAME/KEY: misc_difference
( B ) LOCATION: replace(9..10, "")
( D ) OTHER INFORMATION: /note="This position indicates a formacetal linkage."

( i x ) FEATURE:
( A ) NAME/KEY: misc_difference
( B ) LOCATION: replace(11..12, "")
( D ) OTHER INFORMATION: /note="This position indicates a formacetal linkage."

( i x ) FEATURE:
( A ) NAME/KEY: misc_difference
( B ) LOCATION: replace(13..14, "")
( D ) OTHER INFORMATION: /note="This position indicates a formacetal linkage."

( x i ) SEQUENCE DESCRIPTION: SEQ ID NO:17:

TCTCTCTCTC TTTTT       15

( 2 ) INFORMATION FOR SEQ ID NO:18:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i x ) FEATURE:
( A ) NAME/KEY: misc_difference
( B ) LOCATION: replace(1..2, "")
( D ) OTHER INFORMATION: /note="This position indicates a thioformacetal linkage."

( i x ) FEATURE:
( A ) NAME/KEY: misc_difference
( B ) LOCATION: replace(3..4, "")
( D ) OTHER INFORMATION: /note="This position indicates a thioformacetal linkage."

( i x ) FEATURE:
( A ) NAME/KEY: misc_difference
( B ) LOCATION: replace(5..6, "")
( D ) OTHER INFORMATION: /note="This position indicates a thioformacetal linkage."

( i x ) FEATURE:
( A ) NAME/KEY: misc_difference
( B ) LOCATION: replace(7..8, "")
( D ) OTHER INFORMATION: /note="This position indicates a thioformacetal linkage."

( i x ) FEATURE:
( A ) NAME/KEY: misc_difference
( B ) LOCATION: replace(9..10, "")
( D ) OTHER INFORMATION: /note="This position indicates a thioformacetal linkage."

( i x ) FEATURE:
( A ) NAME/KEY: misc_difference
( B ) LOCATION: replace(11..12, "")
( D ) OTHER INFORMATION: /note="This position indicates a thioformacetal linkage."

( i x ) FEATURE:
( A ) NAME/KEY: misc_difference
( B ) LOCATION: replace(13..14, "")
( D ) OTHER INFORMATION: /note="This position indicates a thioformacetal linkage."

( x i ) SEQUENCE DESCRIPTION: SEQ ID NO:18:

TCTCTCTCTC TTTTT       15